(12) United States Patent
Takanashi et al.

(10) Patent No.: US 9,903,797 B2
(45) Date of Patent: Feb. 27, 2018

(54) STAINING AGENT FOR STAINING TISSUE, PRODUCTION METHOD FOR STAINING AGENT FOR STAINING TISSUE AND TISSUE STAINING KIT INCLUDING STAINING AGENT FOR STAINING TISSUE

(71) Applicant: Konica Minolta, Inc., Tokyo (JP)

(72) Inventors: Kensaku Takanashi, Hino (JP); Yasushi Nakano, Hino (JP); Takeshi Isoda, Sayama (JP); Hideki Gouda, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 14/773,148

(22) PCT Filed: Mar. 6, 2014

(86) PCT No.: PCT/JP2014/055798
§ 371 (c)(1),
(2) Date: Sep. 4, 2015

(87) PCT Pub. No.: WO2014/136885
PCT Pub. Date: Sep. 12, 2014

(65) Prior Publication Data
US 2016/0018300 A1    Jan. 21, 2016

(30) Foreign Application Priority Data
Mar. 8, 2013   (JP) .................................. 2013-047257

(51) Int. Cl.
*A61K 9/00* (2006.01)
*G01N 1/30* (2006.01)
*G01N 33/52* (2006.01)

(52) U.S. Cl.
CPC ............... *G01N 1/30* (2013.01); *G01N 33/52* (2013.01); *G01N 2001/302* (2013.01)

(58) Field of Classification Search
CPC ....................................................... G01N 1/30
See application file for complete search history.

(56) References Cited

U.S. PATENT DOCUMENTS

| 4,326,008 A | 4/1982 | Rembaum |
| 2009/0068639 A1 | 3/2009 | Aizawa et al. |

(Continued)

FOREIGN PATENT DOCUMENTS

| EP | 2613138 A1 | 7/2013 |
| EP | 2613145 A1 | 7/2013 |

(Continued)

OTHER PUBLICATIONS

Jianqiang Qu, et al; Ionic perylenetetracarboxdiimides: highly fluorescent and water-soluble dyes for biolabeling; Angew. Chem. Int. Ed.; 2004; vol. 43; pp. 1528-1531.
Kalliat T. Arun, et al; Near-infrared fluorescent probes: synthesis and spectroscopic investigations of a few amphiphilic squaraine dyes; J. Phys. Chem. A. 2005; vol. 109; pp. 5571-5578.
International Search Report dated Apr. 8, 2014 for PCT/JP2014/055798 and English translation.
Written Opinion of the International Searching Authority and English translation.
Robbins Basic Pathology: With Student Consult Online Access, 9e (Robbins Pathology) Saunders, 2012 (not available).

(Continued)

*Primary Examiner* — Paul Dickinson
(74) *Attorney, Agent, or Firm* — Lucas & Mercanti, LLP

(57) ABSTRACT

An object of the present invention is to provide: a staining agent for tissue staining which has an improved fluorescence signal evaluation accuracy; and a tissue staining kit comprising the staining agent. The staining agent for tissue (Continued)

staining contains, as a staining component, dye-resin particles comprising thermosetting resin particles and a fluorescent dye immobilized on the resin particles, wherein the resin particles contains a substituent having an electric charge opposite to that of the fluorescent dye and forms an ionic bond or a covalent bond with the fluorescent dye, and the dye-resin particles have a particle size variation coefficient of 15% or less.

14 Claims, 2 Drawing Sheets

(56) References Cited

U.S. PATENT DOCUMENTS

| | | |
|---|---|---|
| 2010/0141752 A1 | 6/2010 | Yamada et al. |
| 2010/0272334 A1 | 10/2010 | Yamada et al. |
| 2013/0157287 A1 | 6/2013 | Takanashi et al. |
| 2014/0220598 A1* | 8/2014 | Takanashi .......... G01N 21/6428 435/7.23 |

FOREIGN PATENT DOCUMENTS

| | | |
|---|---|---|
| JP | 2007178315 A | 7/2007 |
| JP | 2009014729 A | 1/2009 |
| JP | 2010018049 A | 1/2010 |
| JP | 2010134195 A | 6/2010 |
| WO | 9323492 A1 | 11/1993 |
| WO | 9937814 A1 | 7/1999 |
| WO | 2012029752 A1 | 3/2012 |

OTHER PUBLICATIONS

Extended European Search Report dated Sep. 27, 2016 from corresponding European Application; Application No./Patent Application No. 14761085.1-1554/2966445 PCT/JP2014055798; Applicant: Konica Minolta, Inc.; Total of 8 pages.

Brian Nevius et al; "Surface-functionalization effects on uptake of fluorescent polystyrene nanoparticles by model biofilms", Ecotoxicology, Kluwer Academic Publishers, BO, vol. 21, No. 8, Jul. 18, 2012, pp. 2205-2213, XP035127716, ISSN: 1573-3017, DOI: 10.1007/S10646-012-0975-3.

Notification of Reasons for Rejection dated Sep. 19, 2017 from corresponding Japanese Patent Application No. JP 2015-504387 and English translation.

* cited by examiner

[Fig. 1]
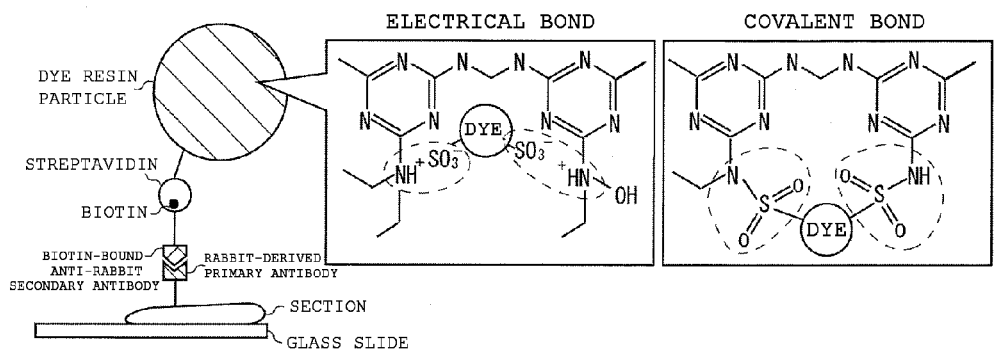
[Fig. 2]
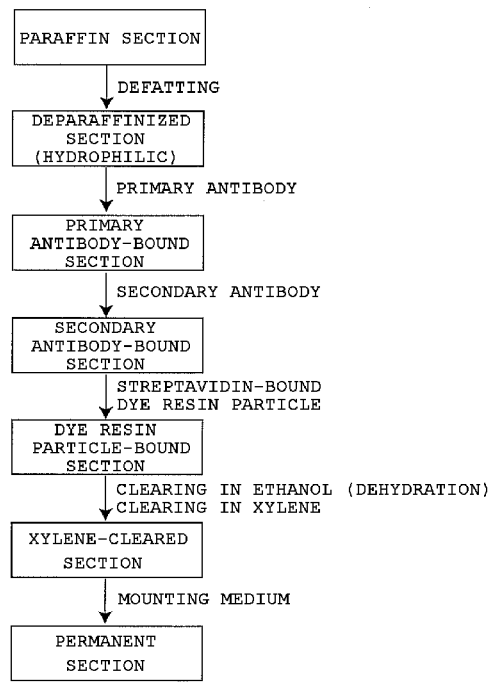

[Fig. 3]

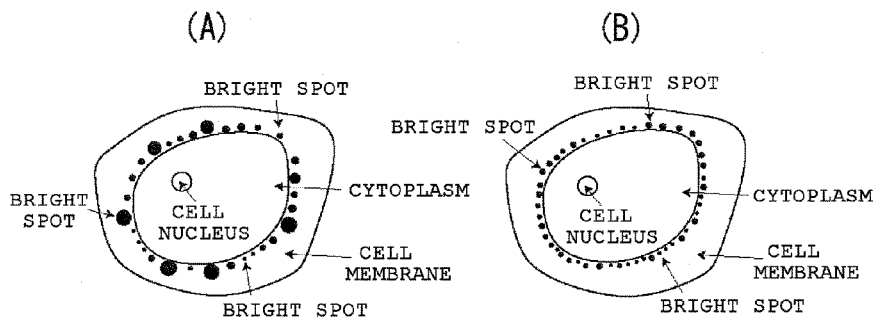

[Fig. 4]

| | (A) POOR VARIATION COEFFICIENT OF PARTICLE SIZE (21% OR LOWER) | (B) GOOD VARIATION COEFFICIENT OF PARTICLE SIZE (12% OR LOWER) |
|---|---|---|
| BRIGHT-FIELD IMAGE | | |
| FLUORESCENCE IMAGE | | |
| | WITH VARIATION IN THE SIZE OF THE BRIGHT SPOTS, IT IS DIFFICULT TO DETERMINE IF EACH BRIGHT SPOT IS FORMED BY A SINGLE PARTICLE OR TWO PARTICLES, MAKING THE MEASUREMENT OF THE NUMBER OF THE BRIGHT SPOTS DIFFICULT. | WITH THE SIZE OF THE BRIGHT SPOTS BEING UNIFORM, THE MEASUREMENT OF THE NUMBER OF THE BRIGHT SPOTS IS EASY. |

US 9,903,797 B2

STAINING AGENT FOR STAINING TISSUE, PRODUCTION METHOD FOR STAINING AGENT FOR STAINING TISSUE AND TISSUE STAINING KIT INCLUDING STAINING AGENT FOR STAINING TISSUE

CROSS REFERENCE TO RELATED APPLICATION

This Application is a 371 of PCT/JP2014/055798 filed on Mar. 6, 2014 which, in turn, claimed the priority of Japanese Patent Application No. JP2013-047257 filed on Mar. 8, 2013, both applications are incorporated herein by reference.

TECHNICAL FIELD

The present invention relates to: a staining agent for tissue staining; a method of producing the staining agent for tissue staining; and a tissue staining kit comprising the staining agent for tissue staining.

BACKGROUND ART

As a medical diagnosis, pathological diagnosis is performed. In the pathological diagnosis, a pathologist diagnoses a disease using a tissue section collected from a human body and informs a clinician of whether or not a therapy and/or surgery is/are necessary. Based on the patient conditions and the pathological diagnosis, a physician determines the pharmacotherapeutic strategies and a surgeon determines whether or not a surgery should be performed.

In pathological diagnosis, it is common practice to prepare a tissue specimen by slicing a tissue sample obtained by evisceration or needle biopsy into a thickness of about several micrometers and then observe the tissue specimen at a magnification under a light microscope so as to obtain various findings. In many cases, a tissue specimen is prepared by fixing a collected tissue through dehydration and paraffin blocking, slicing the thus fixed tissue into a thickness of several micrometers and then removing the paraffin.

In pathological diagnosis, so-called immunostaining is performed for verifying the expression of an antigen or gene to be detected that is contained in a tissue specimen and then immunological observation is performed for diagnosing functional abnormalities such as abnormal expression of a gene or protein.

For immunostaining, for example, a dye staining method using an enzyme (e.g., DAB staining) is employed (Patent Document 1). In DAB staining, an antibody conjugated with peroxidase is used to stain an antigen, and the amount of the antigen is determined by adding thereto diaminobenzidine (DAB), which is the substrate of peroxidase, allowing it to show a color, and then observing the color.

However, in staining with an enzyme such as DAB staining, since the depth of color is largely variable depending on the environmental conditions such as temperature and time, there is a problem that estimation of the actual amount of an antigen or the like based on the depth of color is difficult.

Therefore, for immunological observation in pathological diagnosis, fluorescent labeling using a fluorescent label is performed as an alternative to staining with an enzyme label. This method characteristically has superior quantitative capability than DAB staining (Non-patent Document 1). In this method, the amount of the subject antigen is determined by staining the antigen with an antibody conjugated with a fluorescent dye and observing the stained antigen.

Since a tissue specimen hardly absorbs or scatters light and is thus nearly colorless and transparent, it is sometimes subjected to staining with a dye for morphological observation prior to being observed. There have been proposed a variety of staining techniques. In particular, for tissue specimens, hematoxylin-eosin staining (HE staining) using two dyes, hematoxylin and eosin, is typically used as a staining technique for observing the morphology of the subject tissue (Non-patent Document 1).

Hematoxylin stains cell nuclei, calcareous parts, cartilaginous tissues, bacteria and mucus in livid to light blue, while eosin stains cytoplasm, interstitial tissues, various fibers, erythrocytes and keratinocyte in red to dark red.

A pathologist makes a diagnosis based on the morphological and staining information, such as changes in the size and shape of cell nuclei and changes in the pattern as a tissue, in a micrograph of the stained tissue specimen. Examples of other staining for morphological observation include Papanicolaou staining (Pap staining) used for cytological diagnosis. By subjecting a tissue section to both morphological staining and immunostaining, morphological observation and immunological observation of the specimen also can be performed simultaneously.

In the preparation of a tissue specimen, aqueous mounting media and oil-based mounting media are known as mounting media for mounting a stained pathological section. Aqueous mounting media have a problem in that, since their refractive indices are generally largely different from that of a specimen, it is difficult to make a tissue specimen transparent. Meanwhile, oil-based mounting media are used for producing a permanent preparation not only because their refractive indices are not largely different from that of a tissue specimen and can thus make the tissue specimen transparent, but also because they allow good color tone and color development in morphological staining. Accordingly, oil-based mounting media are preferably used in the preparation of a tissue specimen.

As staining agents for tissue staining that are used in a fluorescent labeling method, staining agents which comprise resin particles containing a fluorescent substance immobilized thereon and which are used in a fluorescent dye labeling method (hereinafter, referred to as "dye-resin particles") are known. In cases where such a staining agent is used for immunostaining of a tissue sample section and the thus stained tissue sample section is observed under a fluorescence microscope to quantify an antigen, the amount of adsorbed dye-resin particles can be evaluated based on the number of bright spots originating from the dye-resin particles.

PRIOR ART REFERENCES

Patent Document

[Patent Document 1] JP-A-2010-134195

Non-Patent Document

[Non-patent Document 1] Robbins Basic Pathology: With STUDENT CONSULT Online Access, 9e (Robbins Pathology) Saunders, (2012)

SUMMARY OF THE INVENTION

Problems to be Solved by the Invention

In the evaluation of the number of bright spots originating from dye-resin particles, variation in the brightness intensity leads to poor accuracy of evaluating a fluorescence signal. The present inventors intensively studied the cause of the variation in the bright spots and, as a result, discovered that variation in the size of the dye-resin particles deteriorates the accuracy of evaluating the fluorescence signal.

Specifically, the brightness of dye-resin particles varies depending on the size of the dye-resin particles; therefore, for example, in the presence of dye-resin particles having such a particle size that yields a brightness of less than a preset fluorescence signal detection threshold, there is a problem that the fluorescence signal that should be naturally detected may not be detected.

Meanwhile, in the presence of dye-resin particles having such a particle size that yields a brightness far exceeding the preset fluorescence signal detection threshold, there is a problem that saturation causes bright spots to fuse with each other and the bright spots cannot thus be distinguished from one another.

Further, in the preparation of a permanent section (see FIG. 2), a tissue section is subjected to clearing where water contained therein is substituted with ethanol/xylene, and this clearing also causes a problem of elution of the fluorescent dye. For example, when a tissue section, which has been stained with a staining agent comprising fluorescent dye-containing uncharged polystyrene particles as dye-resin particles, is cleared, there is a problem that the fluorescent dye bleeds out and this makes it difficult to observe the bright spots, which leads to deterioration of the fluorescence signal evaluation accuracy. Particularly, in the case of a fluorescent dye containing a benzene ring in its chemical structure, since the fluorescent dye is likely to elute into an oil-based mounting medium used for the preparation of a permanent section, there is a problem that this deteriorates the fluorescence signal evaluation accuracy.

The present invention was made in view of the above-described problems, and objects of the present invention are: to provide a staining agent for tissue staining which has an improved fluorescence signal evaluation accuracy; to provide a method of producing the staining agent for tissue staining; and to provide a tissue staining kit comprising the staining agent.

Technical Solution

That is, in order to realize at least one of the above-described objects, the staining agent for tissue staining that reflects one aspect of the present invention is a staining agent for tissue staining which comprises, as a staining component, dye-resin particles containing thermosetting resin particles and a fluorescent dye immobilized on the resin particles, wherein the resin particles contains a substituent having an electric charge opposite to that of the fluorescent dye and thereby forms an ionic bond or a covalent bond with the fluorescent dye, and the dye-resin particles have a particle size variation coefficient of 15% or less.

Further, the method of producing a staining agent for tissue staining that reflects one aspect of the present invention comprises the step of adjusting the variation coefficient of the dye-resin particles to be 15% or less by adding a surfactant to a reaction system used for producing the resin particles through a synthesis reaction.

Moreover, the tissue staining kit reflecting one aspect of the present invention comprises, as a component, any one of the above-described staining agent for tissue staining.

Advantageous Effects of Invention

According to the present invention, by controlling the particle size variation coefficient of the dye-resin particles to be 15% or less, the above-described problem of variation in the bright spots is overcome. In addition, by allowing the fluorescent dye and the thermoplastic resin to form an ionic bond or a covalent bond therebetween, bleeding of the fluorescent dye during fluorescence observation is inhibited. As a result, a staining agent for tissue staining which has an improved fluorescence signal evaluation accuracy, a method of producing the staining agent for tissue staining and a tissue staining kit comprising the staining agent for tissue staining can be provided.

BRIEF DESCRIPTION OF DRAWINGS

FIG. 1 is a drawing that schematically shows the state of a tissue sample section immunostained with the dye-resin particle-containing staining agent for tissue staining according to the present invention and illustrates binding conditions between a resin particle and a dye contained in the dye-resin particle.

FIG. 2 is a drawing that shows the flow of the processes of performing staining, clearing and mounting to prepare the section shown in FIG. 1.

FIG. 3(A) is a drawing that schematically shows a condition where cells of a tissue sample section were immunostained with a conventional staining agent for tissue staining and the fluorescence was observed. FIG. 3(B) is a drawing that schematically shows a condition where cells of a tissue sample section were immunostained with the staining agent for tissue staining according to the present invention and the fluorescence was observed.

FIG. 4(A) shows photographs of cells stained with a secondary antibody labeled with a dye-resin particle according to a Comparative Example. FIG. 4(B) shows photographs of cells stained with a secondary antibody labeled with a dye-resin particle according to an Example.

MODE FOR CARRYING OUT THE INVENTION

The staining agent for tissue staining according to the present invention, the method of producing the staining agent for tissue staining according to the present invention and the tissue staining kit comprising the staining agent for tissue staining according to the present invention will now be described referring to FIGS. 1 to 4.

The staining agent for tissue staining according to the present invention is a staining agent for tissue staining which comprises, as a staining component, dye-resin particles containing thermosetting resin particles and a fluorescent dye immobilized on the resin particles, wherein the dye-resin particles have a particle size variation coefficient of 15% or less.

In the staining agent for tissue staining, the fluorescent dye may be encapsulated in the resin particles. In addition, as the substituent contributing to the ionic bond may be a negatively charged substituent for the fluorescent dye and a positively charged substituent for the resin particles.

The electric charge of the fluorescent dye as a whole and that of the resin particles as a whole may be the same as the electric charge of the respective substituents contributing to the ionic bond. Further, in the fluorescent dye, the ratio, the molecular weight of the fluorescent dye per molecule/the number of charged substituents, may be less than 400 (Molecular weight of the fluorescent dye per molecule/Number of charged substituents <400).

The fluorescent dye may contain at least two negatively charged substituents per molecule. Further, the positively charged substituent may be an amino group, and the negatively charged substituent may be a sulfo group or a carboxyl group.

At least one of the negatively charged substituents of the fluorescent dye may be a sulfo group. Further, the fluorescent dye may be rhodamine, BODIPY, squarylium or an aromatic hydrocarbon-based dye molecule.

The resin particles may be formed using melamine, and the fluorescent dye may be rhodamine or an aromatic hydrocarbon-based dye molecule. Further, the resin particles and the fluorescent dye may be covalently bound with each other through any one of an amide bond, an ester bond, an ether bond and a C—N bond.

The thermosetting resin may contain a structural unit formed from at least one monomer selected from the group consisting of melamine, urea, guanamine, phenol and xylene.

The method of producing a staining agent for tissue staining according to the present invention comprises the step of adjusting the variation coefficient of the dye-resin particles to be 15% or less by adding a surfactant to a reaction system used for producing the resin particles through a synthesis reaction.

The tissue staining kit according to the present invention comprises any one of the above-described staining agent for tissue staining as a component.

<Dye-Resin Particle>

In each dye-resin particle, as shown in FIG. 1, a resin particle and a fluorescent dye are ionically or covalently bound with each other. In the former case, ammonium groups, which are formed by an addition of a proton to amino groups of the resin constituting the resin particle, and sulfo groups of the fluorescent dye are ionically bound with each other to form a dye-resin particle (see the areas defined by dashed lines in the left rectangle of FIG. 1). Meanwhile, in the latter case, amino groups of a moiety derived from the monomer constituting the resin particle and sulfo groups of the fluorescent dye are covalently bound with each other to forma dye-resin particle (see the areas defined by dashed lines in the right rectangle of FIG. 1).

These bonds between the resin particle and the fluorescent dye are each formed between a dye molecule and the inside and/or the outer surface of the resin particle. Those cases shown in FIG. 1 each represents a case where a dye is encapsulated and/or immobilized on the outer surface by an ionic bond or a covalent bond (surface immobilization is not shown in the figure). It is noted here that the bonds formed between the resin particle and the fluorescent dye may include both an ionic bond and a covalent bond.

As a fluorescent dye to be encapsulated in and/or surface-immobilized on the resin particle, any one of the below-described fluorescent dyes may be individually immobilized on the resin particle, or a plurality thereof may be mixed and immobilized on the resin particle. For example, two or more fluorescent dyes each having different excitation wavelength and emission wavelength may be incorporated.

The method of immobilizing a fluorescent dye on the resin particle is not particularly restricted. For introduction of a fluorescent dye to the resin particle, any method can be employed, and examples thereof include a method of synthesizing dye-resin particles by allowing a fluorescent dye molecule to ionically and/or covalently bind to a monomer or oligomer used as the material of the resin particle and then polymerizing the monomer or oligomer; and a method of introducing a dye to pre-produced resin particles by adsorption.

The average particle size of the dye-resin particles is not particularly restricted; however, it is usually 10 to 500 nm, preferably 50 to 200 nm.

Further, in cases where the dye-resin particles are used for immunostaining, as shown in FIG. 1, for example, the dye-resin particles can be used in a constitution where one side of a linker such as streptavidin or biotin is added to the resin particles and the other side of the linker is added to a secondary antibody.

<Thermosetting Resin>

The thermosetting resin constituting the dye-resin particles of the present invention is not particularly restricted as long as the dye-resin particles contains a thermosetting resin capable of immobilizing a fluorescent dye by the above-described ionic bond and/or covalent bond.

In the thermosetting resin used for ionic bonding with a fluorescent dye, at least some of the hydrogens contained in its structural unit are substituted with charged substituents, or a charged moiety is contained as a part of its chemical structure. Meanwhile, in the thermosetting resin used for covalent bonding with a fluorescent dye, regardless of the presence or absence of the above-described charged substituents, the chemical structure partially contains a moiety capable of covalently bonding with the dye, and this moiety can be utilized to form a covalent bond with the dye. The term "charged substituent or moiety" used herein refers to a substituent or a moiety on a chemical structure which is positively or negatively charged when dissolved in water or acidic or basic water.

As the above-described thermosetting resin, one which contains a structural unit formed from at least one monomer selected from the group consisting of melamine, urea, guanamine, phenol, xylene and derivatives of these monomers can be preferably used.

Thereamong, melamine, urea and guanamine are monomers that contain an amino group in a part of its structure as a positively charged substituent. Phenol is a monomer that contains a phenolic hydroxyl group in a part of its structure as a negatively charged substituent. Xylene is a monomer containing no charged substituent or moiety; therefore, xylene can be used for the ionic bonding with a fluorescent dye after substituting some of the hydrogens thereof with a positively charged or negatively charged substituent.

These thermosetting resins can be produced by, in accordance with a known polymerization method, polymerizing monomers containing a charged substituent or moiety or monomers of a thermosetting resin that contain a reactive group forming a covalent bond with a functional group of a fluorescent dye.

A monomer that originally contains a charged substituent in its structure, such as melamine, can be preferably used because it does not require such a substituent to be introduced thereto.

Examples of a negatively charged substituent contained in a monomer of the thermosetting resin include a sulfo group ($—SO_3^-$) and a carboxyl group ($—COO^-$). Further, examples of a positively charged substituent contained in a monomer of the thermosetting resin include an ammonium group ($—NR_3^+$, wherein R is a hydrogen atom or an alkyl group).

As for the method of introducing a charged substituent to a monomer or the like of the thermosetting resin, for example, introduction of a carboxyl group can be directly carried out by Friedel-Crafts reaction, or it may be carried out by converting a carboxyl group-containing alkyl compound and a monomer into a halide and boronic acid and then allowing them to bind with each other through Suzuki coupling reaction or by converting a carboxyl group-containing alkyl compound and a monomer into halides and then allowing them to bind with each other through a coupling reaction such as Grignard reaction.

As for the introduction of a sulfo group, a monomer can be directly sulfonate with fuming sulfuric acid or chorosulfuric acid, or a sulfo group can be introduced by converting a sulfo group-containing alkyl compound and a monomer into a halide and boronic acid and then subjecting them to Suzuki coupling reaction or by converting a sulfo group-containing alkyl compound and a monomer into halides and then subjecting them to a coupling reaction such as Grignard reaction.

As for the introduction of an amino group, a monomer can be nitrated with fuming nitric acid and the resulting nitro group can be converted to an amino group by reduction reaction, or a monomer can be converted to a halide form and then aminated by direct reaction with ammonia or Gabriel reaction. Alternatively, an amino group can also be introduced by converting an amino group-containing alkyl compound and a monomer into a halide and boronic acid and then allowing them to bind with each other through Suzuki coupling reaction or by converting a amino group-containing alkyl compound and a monomer into halides and then allowing them to bind with each other through a coupling reaction such as Grignard reaction.

In the above-described reactions, a carboxyl group, a sulfo group or an amino group may be formed by introducing a protecting group as appropriate, introducing the thus protected carboxyl, sulfo or amino group to a monomer and then performing deprotection.

The molecular structure of the thermosetting resin is a three-dimensional network structure, and this is formed by polymers cross-linking with each other. Therefore, a fluorescent dye encapsulated in the particles of the thermosetting resin is unlikely to elute out of the resin particles, so that an effect of inhibiting the occurrence of blur bright spots in fluorescence observation can be attained.

The thermosetting resin is not restricted to a homopolymer, and it may also be a copolymer. Specifically, the thermosetting resin may be a copolymer obtained by copolymerizing a combination of a plurality of the above-described monomers or oligomers constituting polymelamine or the like, or a copolymer obtained by copolymerizing any of the above-described monomers or oligomers with other monomer or oligomer.

<Fluorescent Dye>

The fluorescent dye used in the present invention may be any existing fluorescent dye. However, it is desirable to use a fluorescent dye which is not adversely affected by heat even under the heating conditions of the synthesis reaction of the thermosetting resin. Such a fluorescent dye can be obtained or prepared by a known method.

In cases where the resin particles and the fluorescent dye are ionically bound, as shown in the left rectangle of FIG. 1, it is preferred that the monomer or oligomer of the resin material and the fluorescent dye have opposite electric charges. This allows the resin material and the dye molecules to associate with each other prior to heat-curing of the resin material, so that the fluorescent dye can be easily incorporated into the resin particles.

By the association between the resin particles and the fluorescent dye, the molecules of the fluorescent dye are immobilized on the resin particles, and this makes the elution of the dye from the resin particles unlikely to occur. When the resin particles and the dye are immobilized with each other in the same association mode, the greater the number of the association sites, the stronger becomes the immobilization between the dye and the resin and, thus, the less likely is the elution of the dye to occur. Therefore, it is preferred that the fluorescent dye have two or more substituents.

Further, the fluorescent dye enters between the substituents of adjacent resin molecules and functions as a cross-linking agent that links them. Consequently, the bond between the resin structural units becomes strong and the bond between the resin particles and the fluorescent dye also becomes strong, and this also makes the elution of the association products of the dye and the resin unlikely to occur. Moreover, since the molecules of the fluorescent dye are stabilized and the heat resistance of the fluorescent dye is thereby further improved, when the resin particles are formed by heat-curing polymerization reaction, the fluorescent dye is hardly adversely affected by the heat and the elution of the fluorescent dye from the resin particles is thus unlikely to occur.

Also in cases where the resin particles and the fluorescent dye are covalently bound, from the same reasons as described above, it is preferred that the fluorescent dye have two or more reactive groups.

The fluorescent dye can be selected from various lines of dye molecules, such as rhodamine-based dye molecules, BODIPY (registered trademark, manufactured by Invitrogen), squarylium-based dye molecules and aromatic hydrocarbon-based dye molecules.

Thereamong, fluorescent dyes such as aromatic ring-containing dye molecules (aromatic hydrocarbon-based dye molecules) and rhodamine-based dye molecules are preferred because of their relatively high light resistance. Particularly, perylene, pyrene and perylene diimide that belong to the aromatic ring-containing dye molecules are preferred. Further, since rhodamine-based dyes and perylene diimide show excellent quantum yield, light absorption and the like and has excellent luminous efficiency, resin particles containing these dyes exhibit superior luminescence intensity than those resin particles containing other dyes Specific examples of the rhodamine-based dye molecules include 5-carboxy-rhodamine, 6-carboxy-rhodamine, 5,6-dicarboxy-rhodamine, rhodamine 6G, tetramethyl rhodamine, X-rhodamine, Texas Red, Spectrum Red, LD700 PERCHLORATE, and derivatives thereof.

Specific examples of the BODIPY-based dye molecules include BODIPY FL, BODIPY TMR, BODIPY 493/503, BODIPY 530/550, BODIPY 558/568, BODIPY 564/570, BODIPY 576/589, BODIPY 581/591, BODIPY 630/650, BODIPY 650/665 (all of which are manufactured by Invitrogen), and derivatives thereof.

Specific examples of the squarylium-based dye molecules include SRfluor 680-carboxylate,
1,3-bis[4-(dimethylamino)-2-hydroxyphenyl]-2,4-dihydroxycyclo butenediylium dihydroxide,
bis,1,3-bis[4-(dimethylamino)phenyl]-2,4-dihydroxycyclobutene diylium dihydroxide,
bis,2-(4-(diethylamino)-2-hydroxyphenyl)-4-(4-(diethyliminio)-2-hydroxycyclohexa-2,5-dienylidene)-3-oxocyclobut-1-enolate,
2-(4-(dibutylamino)-2-hydroxyphenyl)-4-(4-(dibutyliminio)-2-hydroxycyclohexa-2,5-dienylidene)-3-oxocyclobut-1-enolate,
2-(8-hydroxy-1,1,7,7-tetramethyl-1,2,3,5,6,7-hexahydropyrido[3,2,1-ij]quinolin-9-yl)-4-(8-hydroxy-1,1,7,7-tetramethyl-2,3,6,7-tetrahydro-1H-pyrido[3,2,1-ij]quinolinium-9(5H)-ylidene)-3-oxocyclobut-1-enolate, and derivatives thereof.

Specific examples of the aromatic hydrocarbon-based dye molecules include
N,N-bis-(2,6-diisopropylphenyl)-1,6,7,12-(4-tert-butylphenoxy)-perylene-3,4,9,10-tetracarbonacid diimide,
N,N'-bis(2,6-diisopropylphenyl)-1,6,7,12-tetraphenoxyperylene-3,4:9,10-tetracarboxdiimide,
N,N'-bis(2,6-diisopropylphenyl)perylene-3,4,9,10-bis(dicarbimide),
16,N,N'-bis(2,6-dimethylphenyl)perylene-3,4,9,10-tetracarboxylic diimide,
4,4'-[(8,16-dihydro-8,16-dioxodibenzo[a,j]perylene-2,10-diyl)dioxy]dibutyric acid,
2,10-dihydroxy-dibenzo[a,j]perylene-8,16-dione,
2,10-bis(3-aminopropoxy)dibenzo[a,j]perylene-8,16-dione,
3,3'-[(8,16-dihydro-8,16-dioxodibenzo[a,j]perylene-2,10-diyl)dioxy]dipropylamine,
17-bis(octyloxy)anthra[9,1,2-cde-]benzo[rst]pentaphene-5-10-dione, octadecanoic acid,
5,10-dihydro-5,10-dioxoanthra[9,1,2-cde]benzo[rst]pentaphene-16,17-diylester,
dihydroxydibenzanthrone,
benzenesulfonic acid,
4,4',4'',4'''-[[2,9-bis[2,6-bis(1-methylethyl)phenyl]-1,2,3,8,9,10-hexahydro-1,3,8,10-tetraoxoanthra[2,1,9-def:6,5,10-d'e'f']diisoquinoline-5,6,12,13-tetrayl]tetrakis(oxy)] tetrakis-, benzeneethanaminium,
4,4',4'',4'''-[[2,9-bis[2,6-bis(1-methylethyl)phenyl]-1,2,3,8,9,10-hexahydro-1,3,8,10-tetraoxoanthra[2,1,9-def:6,5,10-d'e'f']diisoquinoline-5,6,12,13-tetrayl]tetrakis(oxy)] tetrakis[N,N,N-trimethyl-], and derivatives thereof.

<Method of Producing Dye-Resin Particles>

The dye-resin particles according to the present invention, which have a variation coefficient of 15% or less, preferably less than 15%, can be produced by, for example, the below-described steps. When heat-curing one or more monomers or oligomers to produce the dye-resin particles, the polymerization reaction can be performed in the presence of a prescribed amount of a surfactant. By adding a surfactant having an emulsifying effect in the range of 10 to 60% by weight with respect to the resin material, an arbitrary particle size can be attained and, for example, particles of 30 to 300 nm in size can be prepared. In addition, by increasing the proportion of the surfactant, smaller particles, such as those of 30 nm or smaller in size, can be prepared. Meanwhile, by reducing the proportion of the surfactant, larger particles, such as those of 300 nm or larger in size, can be prepared. In the preparation of the particles, the amount of the surfactant can be arbitrarily changed in the range of 0.1 to 3.0% by weight, preferably 0.25 to 1.0% by weight. The above-described proportion and amount of the surfactant are exemplary and can each be changed in an arbitrary range.

(1) Mixing Step

The mixing step is a step of mixing the above-described fluorescent dye, a surfactant, a proton donor, one or more monomers or oligomers constituting resin particles, and the like.

(Surfactant)

The present inventors discovered that the particle size variation coefficient of the dye-resin particles to be produced varies depending on the molar ratio between the surfactant and the monomer (s) (monomer (s) used as resin constituent(s)) and the type of the surfactant. Therefore, it is required that the type of the surfactant and the molar ratio between the surfactant and the monomer(s) be adjusted to perform the polymerization of the resin, such that the resulting dye-resin particles have a variation coefficient of 15% or less.

As for the type of the surfactant, all of anionic, nonionic and cationic surfactants can be used. Thereamong, for cationic resin monomers, since the degree of the effect of the electric charge of the surfactant on the particle size variation coefficient of the resulting resin particles is in the following relationship: nonionic surfactants>anionic surfactants>cationic surfactants, it is preferred to use an anionic or nonionic surfactant. On the other hand, for anionic resin monomers, since the degree of the effect of the electric charge of the surfactant is in the following relationship: nonionic surfactants>cationic surfactants>anionic surfactants, it is preferred to use a cationic or nonionic surfactant.

As the surfactant, the following ones can be used; however, the surfactant is not restricted thereto. Examples of an anionic surfactant include sodium dodecylbenzenesulfonate. Examples of a nonionic surfactant include polyethylene glycols and polyoxyethylene alkyl ethers. Examples of a cationic surfactant include dodecyltrimethylammonium bromide.

Further, it is preferred to set the weight ratio of the monomer(s) and the surfactant in a polymerization reaction system, monomer(s):surfactant, to be 10:1 to 10:6. As shown in Examples, it is more preferred to set the molar ratio, monomer units:surfactant, to be about 100:1.5 to 100:3.5.

As the surfactant, for example, EMULGEN or NEOPELEX (both are registered trademarks; manufactured by Kao Corporation) can be preferably used. It is noted here that the effective ingredient of EMULGEN is polyoxyethylene alkyl ether and that of NEOPELEX is sodium dodecylbenzenesulfonate. The surfactant forms micelles in which an aqueous phase is arranged outside and an oil phase is arranged inside, and this generates a condition in which the resin-forming monomers are contained in the oil phase arranged inside each micelle, so that polymerization reaction takes place inside the micelles.

As the polymerization reaction proceeds in the oil phase arranged inside the micelles and the monomers in the oil phase start to be depleted, the monomers dispersed in the aqueous phase migrate to the oil phase. In this process, it is believed that the surfactant positioned at the interface between water and oil functions to control the inflow of the monomers from the aqueous phase, thereby allowing the resulting resin particles to have uniform particle size.

When the electric charge of the surfactant positioned at the interface between the oil phase inside the micelles and the aqueous phase in the outer part of the micelles is opposite to the electric charge of the monomers supplied from the aqueous phase to the oil phase, the monomers in the aqueous phase are electrically attracted to the surfactant and the monomers are thus likely to be supplied to the oil phase inside the micelles. Therefore, when cationic monomers are used, an anionic or nonionic surfactant can be preferably used.

Further, as an emulsifier for emulsion polymerization, it is required to select one which has a clouding point higher than the temperature of the heat-curing reaction performed in the polymerization step. This is because, if an emulsifier having a clouding point lower than the heat-curing reaction temperature is selected, the surfactant loses its ability to hydrate with water and becomes dysfunctional, so that resin particles cannot be produced and the resin instead forms aggregates.

(Proton Donor)

In cases where the thermosetting resin and the fluorescent dye are ionically bound, a proton donor which actively supplies $H^+$ and imparts a positive charge to the substituents of the thermosetting resin and fluorescent dye can be used as well. Examples of such a proton donor include formic acid, acetic acid, p-toluenesulfonic acid and their equivalents. When a substituent attached to the dye is an acid such as a carboxylic group or sulfonic group, this substituent is also capable of functioning as a proton donor. Conversely, it is also possible to use a proton acceptor which actively removes $H^+$ and imparts a negative charge to the substituents of the thermosetting resin and fluorescent dye. For example, a base such as sodium hydroxide functions as a proton acceptor.

(Polymerization Reaction Accelerator)

As a reaction accelerator of the thermosetting resin, for example, an acid can be used. Melamine resins, urea resins, xylene resins and phenol resins are all known to be facilitated to react by an acid catalyst. As the acid, for example, formic acid, acetic acid, sulfuric acid, hydrochloric acid, nitric acid, p-toluenesulfonic acid and dodecylbenzenesulfonic acid are known. The reaction of a thermosetting resin can be advanced only by heating; however, since an addition of a reaction accelerator allows the reaction to proceed at a lower temperature, a reaction accelerator can be added in such a range where it is able to control the reaction and the performance.

(2) Polymerization Step

The polymerization step is a step of forming dye-resin particles by heat-curing, that is, polymerizing monomers or oligomers. The reaction conditions (heat-curing temperature and polymerization time) are determined based on the composition of the monomers or oligomers to be polymerized, and the polymerization can be performed in accordance with a known method. Here, the polymerization is required to be performed under the reaction conditions in which the performance of the fluorescent dye is not reduced (within the range of the heat resistant temperature of the fluorescent dye).

For example, when a melamine resin is selected as the thermosetting resin, the synthesis reaction of the melamine resin is performed by heating at 70° C. to 200° C., preferably at 150° C. to 200° C. As for the heat resistant temperatures of fluorescent dyes, the rhodamine-based dye molecules, BODIPY (registered trademark, manufactured by Invitrogen), squarylium-based dye molecules and aromatic hydrocarbon-based dye molecules have a heat resistant temperature of 200° C., 200° C., 200° C. and 300° C. or higher, respectively, and it is required to use a fluorescent dye capable of withstanding the synthesis reaction.

By the polymerization step, the encapsulated fluorescent dye is made unlikely to elute from the dye-resin particles. If the polymerization reaction was insufficient and the problem of the fluorescent dye eluting from the dye-resin particles occurred, the thus produced dye-resin particles may also be subjected to a treatment where the dye-resin particles are further heat-cured by heating in a temperature range that is not higher than the decomposition temperature or melting temperature of the resin and does not adversely affect the dye and the resin particles, that is, the cross-linking between the dye and the resin particles is further facilitated, so as to inhibit the elution of the fluorescent dye.

(3) Washing Step

The washing step is a step of removing impurities, such as excess resin material, excess fluorescent dye and excess emulsifier from the thus obtained dispersion of the dye-resin particles. The washing is performed, for example, as follows: after recovering resin components from the reaction solution by centrifugation and removing the resulting supernatant, ultrapure water is added to the recovered resin components and the resultant is ultrasonicated for re-dispersion of the resin components. It is preferred that such a series of washing operations, which are centrifugation, supernatant removal and re-dispersion into ultrapure water, be repeated plural times until the resulting supernatant no longer shows any absorption or fluorescence emission attributed to the resin or the fluorescent dye.

(4) Addition Step

The addition step is a step of adding a linker or the like for immunostaining to the dye-resin particles. As for the type of the linker to be added to the dye-resin particles, a streptavidin-biotin linker or the like can be used; however, the linker is not restricted thereto.

The addition of the streptavidin-biotin linker exemplified above is performed by, for example, the following method. First, while adding a thiol group to streptavidin using a thiol group-introducing reagent, an amino group is introduced to the surface of the dye-resin particles using an amino group-introducing reagent. Then, the dye-resin particles and streptavidin are linked with each other using a linker which has an active ester reacting with an amino group and a maleimide group reacting with a thiol group at the respective ends, such as PEG.

Examples of the amino group-introducing reagent include aminopropyltrimethoxysilane and the like, and examples of the thiol group-introducing reagent include N-succinimidyl-S-acetylthioacetate. The above-described addition using these reagents can itself be carried out by a known method.

<Verification of Produced Dye-Resin Particles>

(Particle Size of Resin Particles and Variation Coefficient Thereof)

The particle size of the thus produced dye-resin particles can be determined by taking an electron micrograph thereof using a scanning electron microscope (SEM), measuring the cross-sectional area of the dye-resin particle and then determining the particle size as the diameter of a circular area corresponding to the measured value (circular area-equivalent diameter). With regard to the average particle size (average particle diameter) and the variation coefficient of a group of the dye-resin particles, after measuring the particle size for a sufficient number (for example, 300) of the dye-resin particles in the above-described manner, the average particle size is calculated as the arithmetic mean of the measured values, and the variation coefficient is calculated by the following equation:

$$100 \times \text{(standard deviation of particle size)/(average particle size)}.$$

[Tissue Staining]

In the present invention, as a tissue staining method, fluorescent staining in which a biological substance to be detected is stained using the above-described dye-resin particle as a fluorescent label for immunostaining is employed. For example, when immunostaining a specific antigen, the following methods can be employed: a method in which a fluorescent label (conjugate) is prepared by directly binding the dye-resin particle and a primary antibody via the above-described linker and an antigen is then stained (primary antibody method); a method in which a fluorescent label conjugate is prepared by directly binding the dye-resin particle and a secondary antibody, and an antigen is bound with a primary antibody and this primary antibody is then stained (secondary antibody method); a method in which, as described above referring to FIG. 1, a fluorescent label is prepared by directly binding the dye-resin particle with biotin, and an antigen is bound with a primary antibody and this primary antibody is then bound with an avidin- or streptavidin-modified secondary antibody, and this secondary antibody is stained; or a method in which a fluorescent label is prepared in the same manner by directly binding the dye-resin particle with avidin or streptavidin and an antigen is bound with a primary antibody and this primary antibody is then bound with a biotin-modified secondary antibody, and this secondary antibody is stained (biotin-avidin method or sandwich method).

Any primary antibody may be used in the immunostaining, and the primary antibody is variable depending on the subject to be immunostained. For example, when immunostaining is performed using HER2 as an antigen, an anti-HER2 antibody is used. Further, any secondary antibody may be used, and the secondary antibody is variable depending on the primary antibody. Examples thereof include anti-mouse, anti-rabbit, anti-bovine, anti-goat, anti-sheep, anti-dog and anti-chicken antibodies.

For binding of the dye-resin particle with an antibody or biotin, any existing method may be employed. For example, amidation by reaction between amine and carboxylic acid, sulfidation by reaction between maleimide and thiol, imination by reaction between aldehyde and amine, or amination by reaction between epoxy and amine can be used.

Here, the above-described immunostaining is not restricted to tissue staining and can be applied to cell staining as well. Further, the biological substance to be detected is not particularly restricted as long as a substance which specifically binds thereto is present. Typically, a combination of an antigen and an antibody is used as described above; however, it is also possible to use, for example, a combination of a nucleic acid molecule (oligonucleotide or polynucleotide) and a nucleic acid molecule having a sequence hybridizable thereto.

[Fluorescence Observation]

By irradiating the pathological section subjected to tissue staining in the above-described step with an excitation light having a wavelength appropriate for the fluorescent dye of the dye-resin particle, the fluorescence emitted by the fluorescent dye is observed. By this step, a specific biomolecule existing in the pathological section can be detected and this information can be utilized to determine, for example, the appropriateness of applying an antibody pharmaceutical (e.g., Herceptin targeting HER2). For the irradiation of excitation light, the same irradiation means as the one used in ordinary fluorescence observation may be employed. For example, from a laser light source installed in a fluorescence microscope, light having a prescribed wavelength can be selected as required.

Observation of fluorescence may be performed either through the lens barrel of a fluorescence microscope or on a separate display means (e.g., a monitor) showing an image taken by a camera mounted on a fluorescence microscope. Depending on the fluorescent dye, even when the fluorescence cannot be adequately observed visually through the lens barrel of a fluorescence microscope, the fluorescence may be observed on an image taken by a camera in some cases. As required, a filter which selectively allows light having a prescribed wavelength to pass therethrough may also be used.

Here, the brightness of an immunostained portion is represented by a value obtained as an average brightness of the parts stained with a fluorescent label conjugate for immunostaining. Further, the "bright spots" of an immunostained portion means, as shown in FIG. 3, those spots shining at the parts stained with a fluorescent label for immunostaining (see FIGS. 3(A) and 3(B)).

<Tissue Staining Kit>

The tissue staining kit according to the present invention comprises the above-described staining agent for tissue staining as a component. As other components, the tissue staining kit may also contain reagents and the like, such as antibodies relating to immunostaining.

The actions and effects that are attained by the staining agent for tissue staining according to the present invention, the method of producing the staining agent for tissue staining according to the present invention and the tissue staining kit according to the present invention will now be described referring to FIGS. 1 to 4.

(1) When the dye-resin particles have a particle size variation coefficient of 15% or less, the resulting bright spots have uniform size. As a result, in contrast to a case where particles have a variation coefficient of greater than 15%, the bright spots observed in fluorescence observation are uniform in size (see FIGS. 3(A) and 3(B) or FIGS. 4(A) and 4(B) for comparison). Accordingly, all of the fluorescence signals emitted from these bright spots fall within the dynamic range set in the fluorescence observation. This resolves the above-described problems, such as fusion of adjacent bright spots due to saturation, and guarantees that the bright spots are distinguished from one another. Consequently, the fluorescence signal evaluation accuracy is improved.

Since the fluorescent dye, which comprises a positively charged or negatively charged substituent, and the thermosetting resin constituting the resin of the dye-resin particles, which comprises a substituent having an electric charge opposite to that of the fluorescent dye, are ionically bound with each other (see FIG. 1), when a tissue section is stained using the dye-resin particles and subsequently subjected to clearing, the dye contained in the resin particles is not likely to elutes out of the resin particles.

(2) Since the fluorescent dye is contained in the resin particles, the fluorescent dye is not unnecessarily exposed to light, so that decomposition of the fluorescent dye caused by light and a reduction in the performance as a fluorescent label can be inhibited.

(3) Particularly, since the substituent contributing to the above-described ionic bond is a negatively charged substituent in the fluorescent dye and a positively charged substituent in the resin particles, particularly the bleeding of the fluorescent dye in fluorescence observation performed after tissue staining can be inhibited, and the brightness of the stained image can be thereby ensured.

(4) When the electric charge of the fluorescent dye as a whole and that of the resin particles as a whole are different from the electric charge of the substituents contributing to the ionic bond, since the molecules of the fluorescent dye and those of the resin are electrically attracted to each other and the substituents of the respective molecules form ionic bonds, the fluorescent dye is more easily immobilized on the resin.

(5) Since the ratio, the molecular weight of the fluorescent dye per molecule/the number of charged substituents, is less than 400 (<400), as compared to a case where the substituents are contained at any other molecular weight ratio, bleeding of the fluorescent dye in a stained tissue image can be better inhibited and the brightness and the performance balance at the bright spots can be more improved.

(6) Since the fluorescent dye has at least two negatively charged substituents per molecule, as shown in the left rectangle of FIG. 1, the fluorescent dye is immobilized in such a manner that it is sandwiched between plural positively charged substituents of the resin. Further, in some cases, the fluorescent dye is immobilized and functions like a cross-linking agent. As a result, since the fluorescent dye is more strongly immobilized as compared to a case where the fluorescent dye has only one substituent, bleeding of the fluorescent dye in a stained tissue image can be inhibited. In addition, the brightness performance can be ensured, and fusion of the bright spots and the like can be inhibited.

(7 and 8) Since the positively charged substituent is an amino group and the negatively charged substituent is a sulfo group or a carboxyl group, the resin and the fluorescent dye can be strongly bound with each other by allowing the electron pair of the sulfo group ($SO_3^-$) having a strong negative charge to form a coordinate bond with the amino group ($-NH^+-$). For example, a sulfo group-containing fluorescent dye can be strongly bound to an amino group-containing thermosetting resin such as melamine.

(9) Since the fluorescent dye is rhodamine, BODIPY, squarylium or an aromatic hydrocarbon-based dye molecule, by the interaction between the fluorescent dye and a hydrophobic moiety of the resin as well as the ionic bond formed by the substituents, the dye molecule and the resin can be strongly bound with each other. This enables to further inhibit the bleeding of the fluorescent dye in a stained tissue image.

(10 and 12) Since the thermosetting resin is synthesized using melamine and the fluorescent dye is rhodamine or an aromatic hydrocarbon-based dye molecule, by hydrophobic interaction between the benzene rings contained in each of the melamine resin and the rhodamine or aromatic hydrocarbon-based dye molecule as well as the above-described ionic bond between the substituents, the dye molecule and the resin can be more strongly bound with each other. This enables to further inhibit the bleeding of the fluorescent dye in a stained tissue image obtained after the preparation of a tissue section (FIG. 2). Furthermore, rhodamine and aromatic hydrocarbons are preferably used also from the standpoints of the brightness and light resistance.

(11) Since the thermosetting resin and the fluorescent dye are covalently bound with each other through any one of an amide bond, an ester bond, an ether bond and a C—N bond, in the clearing performed after staining a tissue section with the resulting dye-resin particles, the fluorescent dye is encapsulated in the resin particles and thereby strongly maintained; therefore, the bleeding of the fluorescent dye out of the resin particles is inhibited.

(13) By incorporating the step of adjusting the variation coefficient of the resin particles to be 15% or less by adding a prescribed amount of a surfactant to the reaction system used for producing the resin particles through a synthesis reaction, dye-resin particles having a variation coefficient of 15% or less can be produced, and a staining agent for tissue staining that has the above-described effects can be provided.

(14) By the tissue staining kit comprising the above-described staining agent for tissue staining as a component, a tissue staining kit having the above-described effects can be provided.

EXAMPLES

The present invention will now be described in detail by way of examples thereof; however, the present invention is not restricted thereto.
[Dyes]
The dyes used in the following Examples and Comparative Examples are shown in Table 1.

TABLE 1-1

| Compound | Dye skeleton | Charge of dye (substituent) | Compound structural formula | Dye molecular weight | Number of carboxyl groups | Number of sulfo groups | Number of amino groups | Number of covalently bound substituents | Dye molecular weight/Number of charged substituents |
|---|---|---|---|---|---|---|---|---|---|
| 1-1 | Rhodamine | – (sulfo group) | 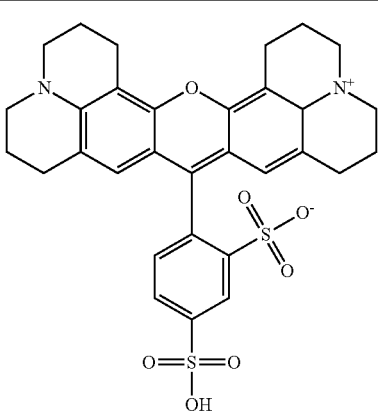 | 578 | 0 | 2 | 0 | 0 | 289 |

TABLE 1-1-continued

| Compound | Dye skeleton | Charge of dye (substituent) | Compound structural formula | Dye molecular weight | Number of carboxyl groups | Number of sulfo groups | Number of amino groups | Number of covalently bound substituents | Dye molecular weight/ Number of charged substituents |
|---|---|---|---|---|---|---|---|---|---|
| 1-2 | Rhodamine | − (sulfo group) | 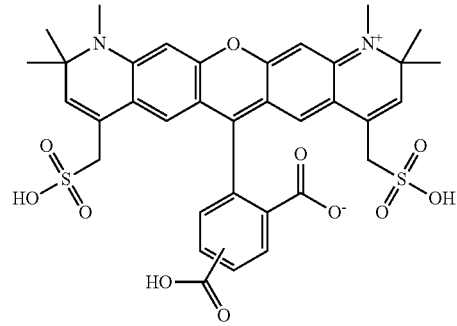 | 693 | 2 | 2 | 0 | 0 | 231 |
| 1-3 | Rhodamine | − (sulfo group) | 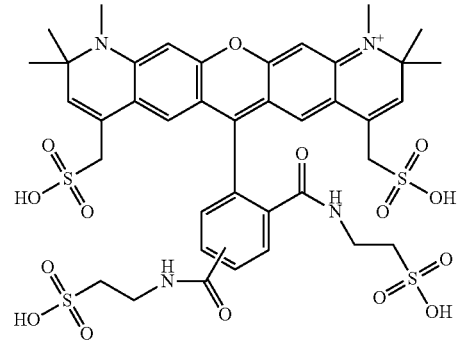 | 924 | 0 | 4 | 0 | 0 | 173 |
| 1-4 | BODIPY | − (sulfo group) | 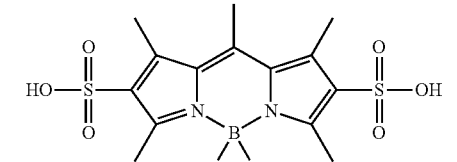 | 397 | 0 | 2 | 0 | 0 | 199 |
| 1-5 | Squarylium | − (carboxyl group) | 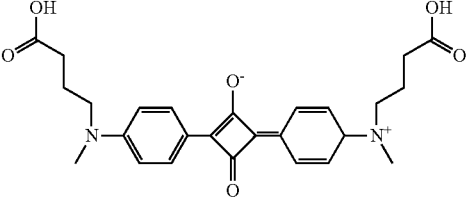 [SMILES: CN(CCCC(=O)O)c1ccc(C2=C([O-])C(=C3C=CC([NH+](C)CCCC(=O)O)C=C3)C2=O)cc1] | 436 | 2 | 0 | 0 | 0 | 218 |
| 1-6 | Pyrene | − (sulfo group) | 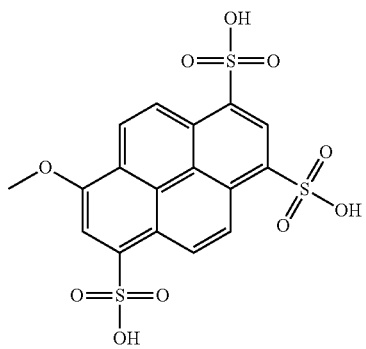 [SMILES: COc1cc(S(=O)(=O)O)c2ccc3c(S(=O)(=O)O)cc(S(=O)(=O)O)c4ccc1c2c43] | 472 | 0 | 3 | 0 | 0 | 157 |

TABLE 1-1-continued

| Compound | Dye skeleton | Charge of dye (substituent) | Compound structural formula | Dye molecular weight | Number of carboxyl groups | Number of sulfo groups | Number of amino groups | Number of covalently bound substituents | Dye molecular weight/ Number of charged substituents |
|---|---|---|---|---|---|---|---|---|---|
| 1-7 | Perylene diimide | − (sulfo group) | | 1,399 | 0 | 4 | 0 | 0 | 350 |
| 1-8 | Perylene diimide | + (ammonium group) | | 1,368 | 0 | 0 | 4 | 0 | 342 |

"−" = negatively charged,
"+" = positively charged

TABLE 1-2

| Compound | Dye skeleton | Charge of dye (substituent) | Compound structural formula | Dye molecular weight | Number of carboxyl groups | Number of sulfo groups | Number of amino groups | Number of covalently bound substituents | Dye molecular weight/ Number of charged substituents |
|---|---|---|---|---|---|---|---|---|---|
| 2-1 | Rhodamine | − (carboxyl group) | | 430 | 1 | 0 | 0 | 0 | 430 |
| 2-2 | Rhodamine | − (sulfo group) | | 605 | 0 | 1 | 0 | 0 | 605 |
| 3-1 | Rhodamine | amide bond | | (632) | 0 | 0 | 0 | 2 | 326 |

TABLE 1-2-continued

| Compound | Dye skeleton | Charge of dye (substituent) | Compound structural formula | Dye molecular weight | Number of carboxyl groups | Number of sulfo groups | Number of amino groups | Number of covalently bound substituents | Dye molecular weight/ Number of charged substituents |
|---|---|---|---|---|---|---|---|---|---|
| 3-2 | Perylene diimide | amide bond | 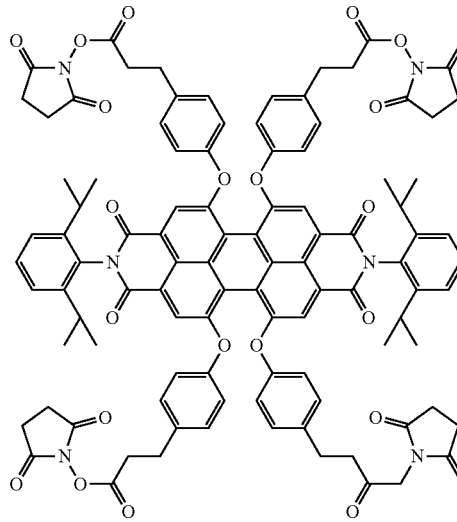 | (1,756) | 0 | 0 | 0 | 4 | 878 |
| 4-1 | Rhodamine | none | 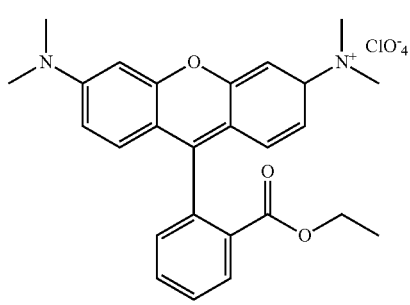 | 403 | 0 | 0 | 0 | 0 | N.D. |
| 4-2 | BODIPY | none | 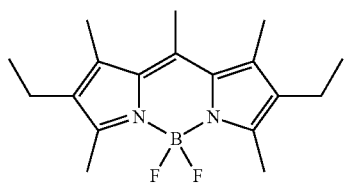 | 293 | 0 | 0 | 0 | 0 | N.D. |
| 4-3 | Squarylium | none | 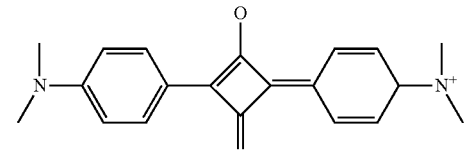 | 291 | 0 | 0 | 0 | 0 | N.D. |

TABLE 1-2-continued

| Compound | Dye skeleton | Charge of dye (substituent) | Compound structural formula | Dye molecular weight | Number of carboxyl groups | Number of sulfo groups | Number of amino groups | Number of covalently bound substituents | Dye molecular weight/Number of charged substituents |
|---|---|---|---|---|---|---|---|---|---|
| 4-4 | Perylene diimide | none | 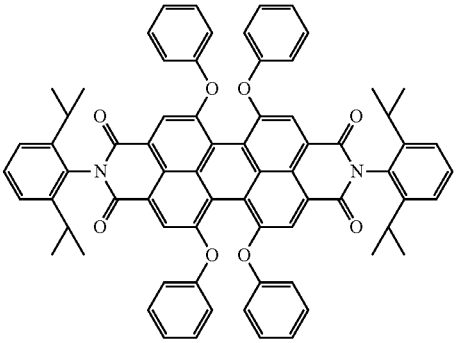 [SMILES: CC(C)c1cccc(C(C)C)c1N1C(=O)c2cc(Oc3ccccc3)c3c4c(Oc5ccccc5)cc5c6c(cc(Oc7ccccc7)c(c7c(Oc8ccccc8)cc(c2c37)C1=O)c64)C(=O)N(c1c(C(C)C)cccc1C(C)C)C5=O] | 1,079 | 0 | 0 | 0 | 0 | N.D. |

"−" = negatively charged,
"+" = positively charged,
"N.D." = no data

TABLE 1-3

| Dye skeleton | Structural formula of dye skeleton | Positively charged substituent of dye skeleton | Negatively charged substituent of dye skeleton |
|---|---|---|---|
| Rhodamine | 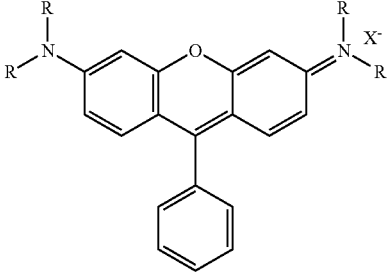 | 1 (ammonium group) | 0 |
| BODIPY | 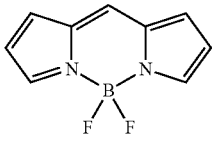 | 0 | 0 |
| Squarylium | 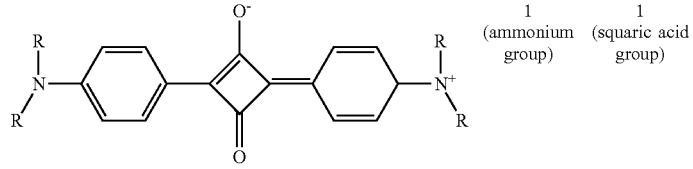 | 1 (ammonium group) | 1 (squaric acid group) |
| Pyrene | 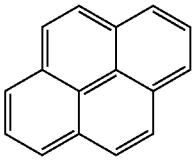 [SMILES: c1cc2ccc3cccc4ccc(c1)c2c34] | 0 | 0 |

TABLE 1-3-continued

| Dye skeleton | Structural formula of dye skeleton | Positively charged substituent of dye skeleton | Negatively charged substituent of dye skeleton |
|---|---|---|---|
| Perylene | [structure of perylene diimide with R—N and N—R groups] | 0 | 0 |

Compounds 1-1 and 4-4 shown in Tables 1-1 to 1-2 are each a dye which has a skeleton of rhodamine, BODIPY, squarylium, pyrene or perylene diimide (see Table 1-3) and contains carboxylic acid, sulfonic acid, an ammonium group and/or a covalently bound moiety as a substituent(s), or a dye containing no such substituent. Particularly, Compounds 1-1 to 1-8 contain carboxyl groups and/or sulfo groups and are each negatively charged as a whole molecule. Compounds 2-1 and 2-2 contain an ammonium group and are each positively charged as a whole molecule. Compounds 3-1 and 3-2 contain covalently bound moieties. Compounds 4-1 to 4-4 have none of the above-described substituents. Here, as shown in Table 1-3, rhodamine contains one ammonium group in its skeleton; however, since the contribution of such a substituent contained in the skeleton is limited, it is not counted in the number of charges (substituents) of each dye. This also applies to squarylium.

[Compound 1-1]

Commercially available Sulforhodamine 101 (manufactured by Sigma-Aldrich) was used.

[Compound 1-2]

A fluorescent dye having a structural formula similar to that of ALEXA 594 was prepared in accordance with the method reported in JP-A-2010-18049 and used as Compound 1-2.

[Compound 1-3]

The above-described Compound 1-2 was esterified with NHS and subsequently allowed to react with 2-aminoethanesulfonic acid (manufactured by Tokyo Chemical Industry Co., Ltd.) in DMF at 90° C. for 1 hour. The resultant was purified by column chromatography and then used as Compound 1-3.

[Compound 1-4]

A commercially available disodium-1,3,5,7,8-pentamethylpyrromethene-2,6-disulfonate-difluoroborate complex (manufactured by Exciton) was used.

[Compound 1-5]

Compound 1-5 was synthesized in accordance with the method described in a literature (J. Phys. Chem. A 2005, 109, 5571).

[Compound 1-6]

Commercially available 8-methoxypyrene-1,3,6-trisulfonic acid trisodium salt (manufactured by Sigma-Aldrich) was used.

[Compounds 1-7, 1-8, 3-1, 3-2 and 4-4]

Compounds 1-7, 1-8, 3-1, 3-2 and 4-4 were each prepared in accordance with the method reported in Angew. Chem. Int. Ed. 2004, 43, 1528.

[Compound 2-1]

Commercially available Rhodamine B (manufactured by Wako Pure Chemical Industries, Ltd.) was used.

[Compound 2-2]

Commercially available Sulforhodamine 101 acid chloride (manufactured by Dojindo Laboratories, Inc.) and ethylamine (manufactured by Tokyo Chemical Industry Co., Ltd.) were allowed to react with each other in DFM at 90° C. for 1 hour. The resultant was purified by column chromatography and then used as Compound 2-2.

[Compound 4-1]

Commercially available tetramethylrhodamine ethyl ester perchlorate (manufactured by Sigma-Aldrich) was used.

[Compound 4-2]

A commercially available 1,3,5,7,8-pentamethyl-2,6-diethylpyrromethene-difluoroborate complex (manufactured by Exiton) was used.

[Compound 4-3]

Commercially available 1,3-bis[4-(dimethylamino)phenyl]-2,4-dihydroxycyclobutene diylium dihydroxide, bis(inner salt) (manufactured by Sigma-Aldrich) was used.

The structures of the above-described compounds are each indicated as an inner salt; however, they may be in a form to which an anion, such as a halide ion, methanesulfonic acid or trifluoromethanesulfonate, is attached as a counter ion. Further, carboxylic acid and sulfonic acid are each indicated in an acid form; however, they may form a salt with an alkali metal or the like. Moreover, the numbers of carboxylic acids, sulfonic acids and ammonium groups are indicated; however, these numbers do not include the number of acids contained in the dye skeleton itself or the number of ammonium salts. For instance, rhodamine contains one ammonium group in its dye skeleton; however, this is not counted. In the same manner, squarylium contains squaric acid and an ammonium group; however, these are also not counted.

Production of Dye-Resin Particles with Variation Coefficient of 15% or Less, in which Fluorescent Dye and Thermosetting Resin are Ionically or Covalently Bound; Tissue Staining, Etc Example 1 (Polymelamine Particle Encapsulating Compound 1-1)

As a fluorescent dye, 14.4 mg of Compound 1-1 (Sulforhodamine 101, manufactured by Sigma-Aldrich) was added and dissolved in 22 mL of water. Then, to the resulting solution, 2 mL of 5% aqueous solution of an emulsifier for emulsion polymerization, EMULGEN (registered trademark) 430 (polyoxyethylene oleyl ether, manufactured by Kao Corporation), was added. This solution was heated to 70° C. with stirring on a hot stirrer, and 0.65 g of a melamine resin material, NIKALAC MX-035 (manufactured by Nippon Carbide Industries Co., Ltd.), was subsequently added.

To the resulting solution, as a surfactant, 1,000 μL of 10% aqueous solution of dodecylbenzenesulfonic acid (manufactured by Kanto Chemical Co., Inc.) was further added, and the resultant was heated with stirring at 70° C. for 50 minutes. Thereafter, the resultant was further heated with stirring at 90° C. for 20 minutes. The resulting dispersion of dye-resin particles was washed with pure water so as to remove impurities such as excess resin material and fluorescent dye.

Specifically, the dispersion was centrifuged at 20,000 G for 15 minutes using a centrifugal machine (micro-refrigerated centrifuge 3740, manufactured by Kubota Corporation) and, after removing the resulting supernatant, the precipitates were re-dispersed in ultrapure water by ultrasonication. The centrifugation, the removal of supernatant and the washing by re-dispersion in ultrapure water were repeated five times. In the thus obtained melamine particles, the melamine resin itself contained a large number of amino groups in its skeleton; therefore, the melamine particles had a positive charge. The charge of the resin particles was evaluated by resin composition analysis using NMR, IR or the like and zeta potential measurement.

Then, 0.1 mg of the thus obtained dye-resin particles were dispersed in 1.5 mL of ethanol, and 2 μL of aminopropyltrimethoxysilane (LS-3150, manufactured by Shin-Etsu Chemical Co., Ltd.) was added thereto. The resulting mixture was allowed to react for 8 hours so as to perform a surface amination treatment, thereby converting the hydroxyl groups existing on the surface of the resin particles to amino groups.

The thus obtained dye-resin particles were adjusted with phosphate-buffered physiological saline (PBS) containing 2 mM of ethylenediamine tetraacetic acid (EDTA) to a concentration of 3 nM. The resulting dispersion of the dye-resin particles having the thus adjusted concentration was mixed with SM(PEG) 12 (succinimidyl-[(N-maleimidopropionamido)-dodecaethylene glycol]ester, manufactured by Thermo Fisher Scientific K.K.) to a final concentration of 10 mM, and the resulting mixture was allowed to react at 20° C. for 1 hour, thereby obtaining a mixture containing the dye-resin particles having a fluorescent dye with terminal maleimide.

This mixture was centrifuged at 10,000 G for 20 minutes and the resulting supernatant was removed. Then, PBS containing 2 mM of EDTA was added to disperse the precipitates, and the resulting dispersion was centrifuged again. The precipitates were washed three times by the same procedure.

(Preparation of Streptavidin)

Meanwhile, streptavidin (manufactured by Wako Pure Chemical Industries, Ltd.) was subjected to a thiol group addition treatment with N-succinimidyl-S-acetylthioacetate (abbreviated as "SATA"), and the resultant was subjected to gel filtration to separately prepare streptavidin capable of binding to the dye-resin particles.

(Binding Between Resin Particles and Streptavidin)

The above-described dye-resin particles and streptavidin were mixed in PBS containing 2 mM of EDTA and allowed to react at room temperature for 1 hour, thereby binding the dye-resin particles with streptavidin. Then, the reaction was terminated by adding 10 mM mercaptoethanol. After concentrating the resulting solution using a centrifugation filter ($\phi$=0.65 μm), unreacted streptavidin and the like were removed using a purification gel-filtration column, thereby obtaining streptavidin-bound dye-resin particles.

(Immunohistological Staining)

Using a staining agent for tissue staining that containing the obtained dye-resin particles, human breast tissue was immunostained. In the staining agent for tissue staining, a buffer such as 1% BSA-containing PBS buffer was used. As a section to be stained, a tissue array slide (manufactured by Cosmo Bio Co., Ltd.; product number: CB-A712) was used. After subjecting the tissue array slide to a deparaffinization treatment, an antigen activation treatment was performed by subjecting the tissue array slide to displacement washing with water and a 15-minute autoclave treatment in 10 mM citrate buffer (pH 6.0). Thereafter, the tissue array slide was washed with PBS buffer, and an anti-HER2 rabbit monoclonal antibody (4B5), which were diluted with 1% BSA-containing PBS buffer to a concentration of 0.05 nM, was allowed to react with the tissue section for 2 hours. After washing the tissue section with PBS, the tissue section was further allowed to react for 30 minutes with a biotin-labeled anti-rabbit antibody diluted with 1% BSA-containing PBS buffer. Thereafter, the tissue section was allowed to react for 2 hours with the staining agent for tissue staining, that is, the streptavidin-containing dye-resin particles produced in the above, and subsequently washed, thereby obtaining an immunohistochemically-stained section. The thus obtained immunohistochemically-stained section was immersed in 4% neutral paraformaldehyde aqueous buffer for 10 minutes to perform an immobilization treatment.

(Morphological Staining)

The thus immobilized immunohistochemically-stained section was subjected to hematoxylin staining and then immersed in ethanol for dehydration. The dehydrated section was cleared by further immersing it in xylene. The section was mounted with a mounting medium and then air-dried to obtain a double-stained section. It is noted here that the hematoxylin staining did not have any effect on the below-described evaluations. Further, when the morphological staining was not performed, the tissue section could be subjected to only the clearing by immersion in ethanol and xylene, or an eosin staining could be added as morphological staining.

(Evaluation of Tissue Image)

Using a commercially available fluorescence microscope, a fluorescence tissue image by the dye-encapsulating resin particles was obtained, and the effect on the measurement of bright spots, the bleeding of the dye in the tissue image and the brightness of the tissue image were evaluated.

The "amount of eluted fluorescent dye" shown in Tables 2 and 4 to 7 is the amount of the dye eluted into ethanol when the dye-resin particles were immersed in ethanol. Specifically, 0.1 mg of the dye-resin particles was immersed in 1 mL of ethanol and subjected to ultrasonication for 10 minutes using a bath-type ultrasonication apparatus (manufactured by AS ONE Corporation). Then, the particles were removed by centrifugation and the resulting supernatant was measured using a fluorophotometer F7000 (manufactured by Hitachi, Ltd.). The amount of eluted fluorescent dye was determined in terms of the amount of dye in 1 mL using a calibration curve prepared in advance based on the dye concentration and the peak value measured by the fluorophotometer. From the thus obtained value, Evaluation 1: the breeding of dye in HER2-stained image can be indirectly analyzed.

In Table 2, with regard to the Evaluation 1, "BB" indicates the absence of bleeding of the fluorescent dye; "CC" indicates that bleeding of the fluorescent dye occurred but the bright spots were recognizable; and "DD" indicates that no bright spot could be verified due to the bleeding of the fluorescent dye.

Further, in Table 2, with regard to the Evaluation 2, "AA" indicates that the HER2-stained image was particularly bright; "BB" means that the bright spots were confirmed in the image at an exposure condition of 400 ms in the fluorescence observation; "CC" means that the bright spots were difficult to see; and "DD" means that no bright spot could be verified.

Moreover, in Table 2, with regard to Evaluation 3, "BB" means that the number of bright spots was measurable in the image for fluorescence observation; "CC" means that the bright spots were difficult to measure; and "DD" means that the bright spots were not measurable. These criteria are also the same for Tables 3 to 7 and other examples.

Example 2 (Polyurea Particle Encapsulating Compound 1-1)

The production of dye-resin particles and the others were carried out in the same manner as in Example 1, except that 0.80 g of a urea resin material was used in place of 0.65 g of the melamine resin material NIKALAC MX-035 (manufactured by Nippon Carbide Industries Co., Ltd.). The thus obtained urea resin contained a large number of amino groups in its skeleton and thus had a positive charge. The urea resin material was urea which was produced by a known method and had a methylolation degree of 40 to 70%.

Example 3 (Polyxylene Particle Encapsulating Compound 1-1)

The production of dye-resin particles and the others were carried out in the same manner as in Example 1, except that 0.80 g of a xylene resin material NIKALAC Y-50 (manufactured by Fudow Co., Ltd.), 0.20 g of butyl isocyanate and 0.20 g of NIKALAC MX-035 (manufactured by Nippon Carbide Industries Co., Ltd.) were used in place of 0.65 g of the melamine resin material NIKALAC MX-035 (manufactured by Nippon Carbide Industries Co., Ltd.). The thus obtained polyxylene resin contained a large number of amino groups and thus had a positive charge.

Examples 4, 7, 10, 13, 16, 19, 24, 27, 30 and 34 (Polymelamine Particles Encapsulating Compounds 1-2 to 3-2)

The production of dye-resin particles and the others were carried out in the same manner as in Example 1, except that Compound 1-1 was changed to Compound 1-2 (Example 4), Compound 1-3 (Example 7), Compound 1-4 (Example 10), Compound 1-5 (Example 13), Compound 1-6 (Example 16), Compound 1-7 (Example 19), Compound 2-1 (Example 24), Compound 2-2 (Example 27), Compound 3-1 (Example 30) or Compound 3-2 (Example 34).

Examples 5, 8, 11, 14, 17, 20, 25, 28, 31 and 35 (Polyurea Particles Encapsulating Compounds 1-2 to 3-2)

The production of dye-resin particles and the like were carried out in the same manner as in Example 2, except that Compound 1-1 was changed to Compound 1-2 (Example 5), Compound 1-3 (Example 8), Compound 1-4 (Example 11), Compound 1-5 (Example 14), Compound 1-6 (Example 17), Compound 1-7 (Example 20), Compound 2-1 (Example 25), Compound 2-2 (Example 28), Compound 3-1 (Example 31) or Compound 3-2 (Example 35).

Examples 6, 9, 12, 15, 18, 21, 26, 29, 33 and 37 (Polyxylene Particles Encapsulating Compounds 1-2 to 3-2)

The production of dye-resin particles and the like were carried out in the same manner as in Example 3, except that Compound 1-1 was changed to Compound 1-2 (Example 6), Compound 1-3 (Example 9), Compound 1-4 (Example 12), Compound 1-5 (Example 15), Compound 1-6 (Example 18), Compound 1-7 (Example 21), Compound 2-1 (Example 26), Compound 2-2 (Example 29), Compound 3-1 (Example 33) or Compound 3-2 (Example 37).

Example 22 (Polyphenol Particle Encapsulating Compound 1-8)

The production of dye-resin particles and the like were carried out in the same manner as in Example 1, except that the fluorescent dye was changed from Compound 1-1 to Compound 1-8; 0.80 g of a phenol resin material NIKANOL PR-1440M (manufactured by Fudow Co., Ltd.) and 0.20 g of phenol were used in place of 0.65 g of the melamine resin material NIKALAC MX-035 (manufactured by Nippon Carbide Industries Co., Ltd.); and the heating with stirring (at 70° C. for 50 minutes) after the addition of 1,000 µL of 10% aqueous solution of dodecylbenzenesulfonic acid (manufactured by Kanto Chemical Co., Inc.) was not performed and the resulting solution was only heated with stirring at 90° C. for 20 minutes, and subsequently heated in an autoclave at 125° C. for 5 minutes. The thus obtained resin particles contained phenol and thus had a negative charge.

Example 23 (Polyxylene Particle Encapsulating Compound 1-8)

The production of dye-resin particles and the others were carried out in the same manner as in Example 1, except that Compound 1-1 was changed to Compound 1-8; 0.20 g of a xylene resin material NIKANOL Y-50 (manufactured by Fudow Co., Ltd.), 0.20 g of a phenol resin material NIKANOL PR-1440M (manufactured by Fudow Co., Ltd.) and 0.20 g of 3-(4 hydroxyphenyl)propionic acid were used in place of 0.65 g of the melamine resin material NIKALAC MX-035 (manufactured by Nippon Carbide Industries Co., Ltd.); and the heating with stirring (at 70° C. for 50 minutes) after the addition of 1,000 µL of 10% aqueous solution of dodecylbenzenesulfonic acid (manufactured by Kanto Chemical Co., Inc.) was not performed and the resulting solution was only heated with stirring at 90° C. for 20 minutes, before heated in an autoclave at 125° C. for 5 minutes. The thus obtained resin particles contained a phenyl group and a carboxyl group and thus had a negative charge.

Examples 32 and 36 (Polyphenol Particles Encapsulating Compound 3-1 or Compound 3-2)

The production of dye-resin particles and the like were carried out in the same manner as in Example 22, except that Compound 1-8 was changed to Compound 3-1 (Example 32) or Compound 3-2 (Example 36).

TABLE 2

| | Dye code (Compound) | Dye electric charge | Substituent of dye | Dye molecular weight | Number of substituents | Dye molecular weight/ Number of charged substituents | Resin type | Resin charge |
|---|---|---|---|---|---|---|---|---|
| Example 1 | 1-1 | − | sulfo group | 578 | 2 | 289 | polymelamine | + |
| Example 2 | | | | | | | polyurea | + |
| Example 3 | | | | | | | polyxylene | + |
| Example 4 | 1-2 | − | sulfo group | 693 | 4 | 173 | polymelamine | + |
| Example 5 | | | | | | | polyurea | + |
| Example 6 | | | | | | | polyxylene | + |
| Example 7 | 1-3 | − | sulfo group | 924 | 4 | 231 | polymelamine | + |
| Example 8 | | | | | | | polyurea | + |
| Example 9 | | | | | | | polyxylene | + |
| Example 10 | 1-4 | − | sulfo group | 397 | 2 | 199 | polymelamine | + |
| Example 11 | | | | | | | polyurea | + |
| Example 12 | | | | | | | polyxylene | + |
| Example 13 | 1-5 | − | carboxyl group | 436 | 2 | 218 | polymelamine | + |
| Example 14 | | | | | | | polyurea | + |
| Example 15 | | | | | | | polyxylene | + |
| Example 16 | 1-6 | − | sulfo group | 472 | 3 | 157 | polymelamine | + |
| Example 17 | | | | | | | polyurea | + |
| Example 18 | | | | | | | polyxylene | + |
| Example 19 | 1-7 | − | sulfo group | 1,398 | 4 | 350 | polymelamine | + |
| Example 20 | | | | | | | polyurea | + |
| Example 21 | | | | | | | polyxylene | + |
| Example 22 | 1-8 | + | ammonium group | 1,366 | 4 | 342 | polyphenol | − |
| Example 23 | | | | | | | polyxylene | − |
| Example 24 | 2-1 | − | carboxyl group | 430 | 1 | 430 | polymelamine | + |
| Example 25 | | | | | | | polyurea | + |
| Example 26 | | | | | | | polyxylene | + |
| Example 27 | 2-2 | − | sulfo group | 605 | 1 | 605 | polymelamine | + |
| Example 28 | | | | | | | polyurea | + |
| Example 29 | | | | | | | polyxylene | + |
| Example 30 | 3-1 | none | amide bond (covalent bond) | 632 | 2 | 316 | polymelamine | + |
| Example 31 | | | | | | | polyurea | + |
| Example 32 | | | | | | | polyphenol | − |
| Example 33 | | | | | | | polyxylene | + |
| Example 34 | 3-2 | none | amide bond (covalent bond) | 1,756 | 4 | 439 | polymelamine | + |
| Example 35 | | | | | | | polyurea | + |
| Example 36 | | | | | | | polyphenol | − |
| Example 37 | | | | | | | polyxylene | + |

| | Amount of eluted dye | Variation coefficient of dye-resin particle [%] | Evaluation 1: Bleeding of dye in HER2-stained image | Evaluation 2: Brightness of HER2-stained image | Evaluation 3: Measurement of bright spots |
|---|---|---|---|---|---|
| Example 1 | 4 | 10 | CC | BB | BB |
| Example 2 | 4 | 13 | CC | BB | BB |
| Example 3 | 6 | 11 | CC | BB | BB |
| Example 4 | 1 | 10 | BB | BB | BB |
| Example 5 | 1 | 10 | BB | BB | BB |
| Example 6 | 2 | 11 | BB | BB | BB |
| Example 7 | 1 | 11 | BB | BB | BB |
| Example 8 | 1 | 10 | BB | BB | BB |
| Example 9 | 1 | 12 | BB | BB | BB |
| Example 10 | 1 | 12 | BB | BB | BB |
| Example 11 | 1 | 11 | BB | BB | BB |
| Example 12 | 1 | 13 | BB | BB | BB |
| Example 13 | 10 | 10 | CC | CC | BB |
| Example 14 | 10 | 10 | CC | CC | BB |
| Example 15 | 14 | 12 | CC | CC | BB |
| Example 16 | 1 | 10 | BB | BB | BB |
| Example 17 | 1 | 10 | BB | BB | BB |
| Example 18 | 1 | 12 | BB | BB | BB |
| Example 19 | 0 | 10 | BB | AA | BB |
| Example 20 | 0 | 10 | BB | BB | BB |
| Example 21 | 0 | 12 | BB | BB | BB |
| Example 22 | 14 | 12 | CC | CC | BB |
| Example 23 | 19 | 14 | CC | CC | BB |
| Example 24 | 21 | 15 | CC | CC | BB |
| Example 25 | 21 | 13 | CC | CC | BB |
| Example 26 | 29 | 14 | CC | CC | BB |
| Example 27 | 18 | 10 | CC | CC | BB |

TABLE 2-continued

| | | | | | |
|---|---|---|---|---|---|
| Example 28 | 18 | 10 | CC | CC | BB |
| Example 29 | 24 | 11 | CC | CC | BB |
| Example 30 | 0 | 10 | BB | CC | BB |
| Example 31 | 0 | 10 | BB | CC | BB |
| Example 32 | 0 | 11 | BB | CC | BB |
| Example 33 | 0 | 11 | BB | CC | BB |
| Example 34 | 0 | 12 | BB | CC | BB |
| Example 35 | 0 | 12 | BB | CC | BB |
| Example 36 | 0 | 12 | BB | CC | BB |
| Example 37 | 0 | 13 | BB | CC | BB |

(Discussion)

Since the fluorescent dyes and the resins had opposite electric charges and the resulting dye-resin particles all had a variation coefficient of 15% or less, bleeding of the fluorescent dyes during fluorescence observation was hardly observed, and good results were obtained in the measurements of the brightness and the bright spots (Examples 1 to 37).

Tissue Staining Etc. With Fluorescent Dye Particles Prepared Using Thermoplastic Resin or Semiconductor Comparative Examples 1 and 2

Immunohistological staining and morphological staining were carried out in the same manner as in Example 1, except that dye-resin particles made of commercially available polystyrene (manufactured by Invitrogen) containing an amino group attached to an end (Comparative Example 1) or commercially available semiconductor nanoparticles containing an amino group attached to an end, "Q-dot" (Comparative Example 2) were used in place of the dye-resin particles produced in Example 1.

Dye-Resin Particles with Variation Coefficient of Greater than 15%; Formed from Fluorescent Dye and Thermosetting Resin with Various Electric Charges Comparative Example 3 (Polymelamine Particle Encapsulating Compound 1-1)

As a fluorescent dye, 2.5 mg of Compound 1-1 (Sulforhodamine 101, manufactured by Sigma-Aldrich) was added to and dissolved in 22.5 mL of water. After heating the resulting solution to 70° C. on a hot stirrer, 1.5 g of a melamine resin NIKALAC MX-035 (manufactured by Nippon Carbide Industries Co., Ltd.) was added, and the resultant was heated with stirring for 5 minutes. Then, 100 µL of formic acid was further added, and the resultant was heated with stirring at 70° C. for 20 minutes and subsequently cooled to room temperature. Thereafter, the resulting reaction mixture was placed in a centrifuge tube and centrifuged for 20 minutes using a centrifugal machine at 20,000 G. After removing the resulting supernatant, the precipitates were re-dispersed in ultrapure water by ultrasonication. The centrifugation, the removal of supernatant and the washing by

TABLE 3

| | | | | Evaluation | | |
|---|---|---|---|---|---|---|
| | Particle name | Amount of eluted dye | Variation coefficient of particles [%] | Evaluation 1: Bleeding of dye in HER2-stained image | Evaluation 2: Brightness of HER2-stained image | Evaluation 3: Measurement of bright spots |
| Comparative Example 1 | Polystyrene particle, manufactured by Invitrogen | 200 | 10 | DD | DD not measurable | DD not measurable |
| Comparative Example 2 | "Q-dot" manufactured by Invitrogen | 0 | 10 | BB | DD | DD not measurable |

(Discussion)

In Comparative Example 1, dye-resin particles obtained by immobilizing a fluorescent dye on the particles of polystyrene, which is a thermoplastic resin, were used. As a result, elution of the dye occurred and, in the Evaluation 3 of the resulting tissue image, the tissue image could not be clearly seen due to bleeding of the dye.

Further, although the commercially available semiconductor nanoparticles "Q-dot" have a variation coefficient of 10% or less, since "Q-dot" itself has a low brightness, the resulting stained image was not observable (Comparative Example 2).

re-dispersion in ultrapure water was repeated five times. The resulting melamine resin particles characteristically had a greater variation coefficient than the particles prepared in Example 1. Using the thus obtained dye-resin particles, immunohistological staining and morphological staining were carried out in the same manner as in Example 1.

Comparative Example 4 (Polyurea Particle Encapsulating Compound 1-1)

Dye-resin particles were produced in the same manner as in Example 3, except that 1.6 g of urea resin material was used in place of 1.5 g of the melamine resin material NIKALAC MX-035 (manufactured by Nippon Carbide Industries Co., Ltd.) in Comparative Example 3. The urea resin material was urea which was produced by a known method and had a methylolation degree of 40 to 70%.

Comparative Example 5 (Polyxylene Particle Encapsulating Compound 1-1)

The production of dye-resin particles and the others were carried out in the same manner as in Example 3, except that 0.80 g of a phenol resin material K-100 (manufactured by Fudow Co., Ltd.) and 0.20 g of 3,5-dimethylaniline were used in place of 1.5 g of the melamine resin material NIKALAC MX-035 (manufactured by Nippon Carbide Industries Co., Ltd.) in Comparative Example 3. The thus obtained xylene resin contained a large number of amino groups and thus had a positive charge.

Comparative Examples 6, 9, 12, 15, 18, 21, 26, 29, 32 and 36 (Polymelamine Particles Encapsulating Compounds 1-2 to 3-2)

The production of dye-resin particles and the others were carried out in the same manner as in Comparative Example 3, except that Compound 1-1 was changed to Compound 1-2 (Comparative Example 6), Compound 1-3 (Comparative Example 9), Compound 1-4 (Comparative Example 12), Compound 1-5 (Comparative Example 15), Compound 1-6 (Comparative Example 18), Compound 1-7 (Comparative Example 21), Compound 2-1 (Comparative Example 26), Compound 2-2 (Comparative Example 29), Compound 3-1 (Comparative Example 32) or Compound 3-2 (Comparative Example 36).

Comparative Examples 7, 10, 13, 16, 19, 22, 27, 30, 33 and 37 (Polyurea Particles Encapsulating Compounds 1-2 to 3-2)

The production of dye-resin particles and the like were carried out in the same manner as in Comparative Example 4, except that Compound 1-1 was changed to Compound 1-2 (Comparative Example 7), Compound 1-3 (Comparative Example 10), Compound 1-4 (Comparative Example 13), Compound 1-5 (Comparative Example 16), Compound 1-6 (Comparative Example 19), Compound 1-7 (Comparative Example 22), Compound 1-8 (Comparative Example 27), Compound 2-1 (Comparative Example 30), Compound 2-2 (Comparative Example 33) or Compound 3-1 (Comparative Example 37).

Comparative Examples 8, 11, 14, 17, 20, 23, 28, 31, 35 and 39 (Polyxylene Particles Encapsulating Compounds 1-2 to 3-2)

The production of dye-resin particles and the others were carried out in the same manner as in Comparative Example 5, except that Compound 1-1 was changed to Compound 1-2 (Comparative Example 8), Compound 1-3 (Comparative Example 11), Compound 1-4 (Comparative Example 14), Compound 1-5 (Comparative Example 17), Compound 1-6 (Comparative Example 20), Compound 1-7 (Comparative Example 23), Compound 2-1 (Comparative Example 28), Compound 2-2 (Comparative Example 31), Compound 3-1 (Comparative Example 35) or Compound 3-2 (Comparative Example 39).

Comparative Example 24 (Polyphenol Particle Encapsulating Compound 1-8)

The production of dye-resin particles and the others were carried out in the same manner as in Comparative Example 3, except that Compound 1-1 was changed to Compound 1-8; 0.80 g of a phenol resin material NIKANOL PR-1440M (manufactured by Fudow Co., Ltd.) and 0.20 g of phenol were used in place of 1.5 g of the melamine resin material NIKALAC MX-035 (manufactured by Nippon Carbide Industries Co., Ltd.); and the heating with stirring (at 70° C. for 50 minutes) after the addition of 1,000 μL of 10% aqueous solution of dodecylbenzenesulfonic acid (manufactured by Kanto Chemical Co., Inc.) was not performed and the resulting solution was only heated with stirring at 90° C. for 20 minutes, subsequently heated in an autoclave at 125° C. for 5 minutes. The thus obtained resin particles contained hydroxyphenyl group and had a negative charge as a whole molecule.

Comparative Example 25 (Polyxylene Particle Encapsulating Compound 1-8)

The production of dye-resin particles and the others were carried out in the same manner as in Comparative Example 3, except that Compound 1-1 was changed to Compound 1-8; 0.80 g of a phenol resin material NIKANOL PR-1440 (manufactured by Fudow Co., Ltd.) and 0.20 g of phenol were used in place of 1.5 g of the melamine resin material NIKALAC MX-035 (manufactured by Nippon Carbide Industries Co., Ltd.); and the heating with stirring (at 70° C. for 50 minutes) after the addition of 1,000 μL of 10% aqueous solution of dodecylbenzenesulfonic acid (manufactured by Kanto Chemical Co., Inc.) was not performed and the resulting solution was only heated with stirring at 90° C. for 20 minutes, subsequently heated in an autoclave at 125° C. for 5 minutes. The thus obtained resin particles contained hydroxyphenyl group and a carboxyl group and had a negative charge as a whole molecule.

Comparative Examples 34 and 38

The production of dye-resin particles, morphological staining and the others were carried out in the same manner as in Comparative Example 24, except that Compound 1-8 was changed to Compound 3-1 (Comparative Example 34) or Compound 3-2 (Comparative Example 38).

TABLE 4

| | Dye code (Compound) | Dye electric charge | Substituent of dye | Dye molecular weight | Number of substituents | Dye molecular weight/ Number of charged substituents | Resin type | Resin charge |
|---|---|---|---|---|---|---|---|---|
| Comparative Example 3 | 1-1 | − | sulfo group | 578 | 2 | 289 | polymelamine | + |
| Comparative Example 4 | | | | | | | polyurea | + |
| Comparative Example 5 | | | | | | | polyxylene | + |
| Comparative Example 6 | 1-2 | − | sulfo group carboxyl group | 693 | 4 | 173 | polymelamine | + |
| Comparative Example 7 | | | | | | | polyurea | + |
| Comparative Example 8 | | | | | | | polyxylene | + |
| Comparative Example 9 | 1-3 | − | sulfo group | 924 | 4 | 231 | polymelamine | + |
| Comparative Example 10 | | | | | | | polyurea | + |
| Comparative Example 11 | | | | | | | polyxylene | + |
| Comparative Example 12 | 1-4 | − | sulfo group | 397 | 2 | 199 | polymelamine | + |
| Comparative Example 13 | | | | | | | polyurea | + |
| Comparative Example 14 | | | | | | | polyxylene | + |
| Comparative Example 15 | 15 | − | carboxyl group | 436 | 2 | 218 | polymelamine | + |
| Comparative Example 16 | | | | | | | polyurea | + |
| Comparative Example 17 | | | | | | | polyxylene | + |
| Comparative Example 18 | 1-6 | − | sulfo group | 472 | 3 | 157 | polymelamine | + |
| Comparative Example 19 | | | | | | | polyurea | + |
| Comparative Example 20 | | | | | | | polyxylene | + |
| Comparative Example 21 | 1-7 | − | sulfo group | 1,398 | 4 | 350 | polymelamine | + |
| Comparative Example 22 | | | | | | | polyurea | + |
| Comparative Example 23 | | | | | | | polyxylene | + |
| Comparative Example 24 | 1-8 | + | ammonium group | 1,366 | 4 | 342 | polyphenol | − |
| Comparative Example 25 | | | | | | | polyxylene | − |
| Comparative Example 26 | 2-1 | − | carboxyl group | 430 | 1 | 430 | polymelamine | + |
| Comparative Example 27 | | | | | | | polyurea | + |
| Comparative Example 28 | | | | | | | polyxylene | + |
| Comparative Example 29 | 2-2 | − | sulfo group | 605 | 1 | 605 | polymelamine | + |
| Comparative Example 30 | | | | | | | polyurea | + |
| Comparative Example 31 | | | | | | | polyxylene | + |
| Comparative Example 32 | 3-1 | none | amide bond (covalent bond) | 632 | 2 | 316 | polymelamine | + |
| Comparative Example 33 | | | | | | | polyurea | + |
| Comparative Example 34 | | | | | | | polyphenol | − |
| Comparative Example 35 | | | | | | | polyxylene | + |
| Comparative Example 36 | 3-2 | none | amide bond (covalent bond) | 1,754 | 4 | 439 | polymelamine | + |
| Comparative Example 37 | | | | | | | polyurea | + |
| Comparative Example 38 | | | | | | | polyphenol | − |

TABLE 4-continued

| | | | | polyxylene | + |
|---|---|---|---|---|---|
| Comparative Example 39 | | | | | |

| | | Variation coefficient of dye-resin particle [%] | Evaluation | | |
|---|---|---|---|---|---|
| | Amount of eluted dye | | Evaluation 1: Bleeding of dye in HER2-stained image | Evaluation 2: Brightness of HER2-stained image | Evaluation 3: Measurement of bright spots |
| Comparative Example 3 | 4 | 22 | CC | BB | DD |
| Comparative Example 4 | 5 | 27 | CC | BB | DD |
| Comparative Example 5 | 6 | 25 | CC | BB | DD |
| Comparative Example 6 | 2 | 23 | BB | BB | DD |
| Comparative Example 7 | 2 | 32 | BB | BB | DD |
| Comparative Example 8 | 3 | 27 | BB | BB | DD |
| Comparative Example 9 | 1 | 22 | BB | BB | DD |
| Comparative Example 10 | 1 | 24 | BB | BB | DD |
| Comparative Example 11 | 1 | 23 | BB | BB | DD |
| Comparative Example 12 | 1 | 22 | BB | BB | DD |
| Comparative Example 13 | 1 | 28 | BB | BB | DD |
| Comparative Example 14 | 1 | 26 | BB | BB | DD |
| Comparative Example 15 | 10 | 25 | CC | CC | DD |
| Comparative Example 16 | 11 | 34 | CC | CC | DD |
| Comparative Example 17 | 14 | 29 | CC | CC | DD |
| Comparative Example 18 | 1 | 20 | BB | BB | DD |
| Comparative Example 19 | 1 | 31 | BB | BB | DD |
| Comparative Example 20 | 1 | 28 | BB | BB | DD |
| Comparative Example 21 | 0 | 21 | BB | BB | DD |
| Comparative Example 22 | 0 | 32 | BB | BB | DD |
| Comparative Example 23 | 0 | 31 | BB | BB | DD |
| Comparative Example 24 | 15 | 27 | CC | CC | DD |
| Comparative Example 25 | 19 | 32 | CC | CC | DD |
| Comparative Example 26 | 21 | 25 | CC | CC | DD |
| Comparative Example 27 | 21 | 30 | CC | CC | DD |
| Comparative Example 28 | 29 | 30 | CC | CC | DD |
| Comparative Example 29 | 18 | 26 | CC | CC | DD |
| Comparative Example 30 | 18 | 31 | CC | CC | DD |
| Comparative Example 31 | 25 | 31 | CC | CC | DD |
| Comparative Example 32 | 0 | 25 | BB | CC | DD |
| Comparative Example 33 | 0 | 27 | BB | CC | DD |
| Comparative Example 34 | 0 | 32 | BB | CC | DD |
| Comparative Example 35 | 0 | 33 | BB | CC | DD |
| Comparative Example 36 | 0 | 26 | BB | CC | DD |

TABLE 4-continued

|  |  |  |  |  |  |
|---|---|---|---|---|---|
| Comparative Example 37 | 0 | 27 | BB | CC | DD |
| Comparative Example 38 | 0 | 31 | BB | CC | DD |
| Comparative Example 39 | 0 | 33 | BB | CC | DD |

(Discussion)

Even the dye-resin particles in which the fluorescent dye and the resin had opposite electric charges showed variations in the particle size and, when the variation coefficient exceeded 15%, the measurement of the bright spots and the like were difficult (Comparative Examples 3 to 39).

Dye-Resin Particles with Variation Coefficient of 15% or Less; Formed from Non-Charged Fluorescent Dye and Positively Charged Resin Comparative Examples 40, 43, 46 and 49
(Polymelamine Particles Encapsulating Compounds 4-1 to 4-4)

The production of dye-resin particles and the others were carried out in the same manner as in Example 1, except that Compound 1-1 was changed to non-charged Compound 4-1 (Comparative Example 40), Compound 4-2 (Comparative Example 43), Compound 4-3 (Comparative Example 46) or Compound 4-4 (Comparative Example 49).

In other words, Comparative Examples 40, 43, 46 and 49 are examples where dye-resin particles having a variation coefficient of 15% or less, in which a non-charged fluorescent dye (Compounds 4-1 to 4-4) was encapsulated in urea resin particles, were produced to perform immunohistological staining, morphological staining, evaluation of a tissue image and the others.

Comparative Examples 41, 44, 47 and 50
(Polyurea Particles Encapsulating Compounds 4-1 to 4-4)

The production of dye-resin particles and the others were carried out in the same manner as in Example 2, except that Compound 1-1 was changed to non-charged Compound 4-1 (Comparative Example 41), Compound 4-2 (Comparative Example 44), Compound 4-3 (Comparative Example 47) or Compound 4-4 (Comparative Example 50).

In other words, Comparative Examples 41, 44, 47 and 50 are examples where a non-charged fluorescent dye (Compound 4-1 to 4-4) was immobilized with polyurea resin particles having a variation coefficient of 15% or less.

Comparative Example 42, 45, 48 and 51
(Polyxylene Particles Encapsulating Compounds 4-1 to 4-4)

The production of dye-resin particles and the others were carried out in the same manner as in Example 3, except that Compound 1-1 was changed to non-charged Compound 4-1 (Comparative Example 42), Compound 4-2 (Comparative Example 45), Compound 4-3 (Comparative Example 48) or Compound 4-4 (Comparative Example 51).

In other words, Comparative Examples 42, 45, 48 and 51 are examples where a non-charged fluorescent dye (Compound 4-1 to 4-4) was immobilized with polyxylene resin particles having a variation coefficient of 15% or less.

TABLE 5

|  | Dye code (Compound) | Dye electric charge | Substituent of dye | Dye molecular weight | Number of substituents | Dye molecular weight/Number of charged substituents | Resin type | Resin charge |
|---|---|---|---|---|---|---|---|---|
| Comparative Example 40 | 4-1 | none | none | 0 | 0 | none | polymelamine | + |
| Comparative Example 41 |  |  |  |  |  |  | polyurea | + |
| Comparative Example 42 |  |  |  |  |  |  | polyxylene | + |
| Comparative Example 43 | 4-2 | none | none | 0 | 0 | none | polymelamine | + |
| Comparative Example 44 |  |  |  |  |  |  | polyurea | + |
| Comparative Example 45 |  |  |  |  |  |  | polyxylene | + |
| Comparative Example 46 | 4-3 | none | none | 0 | 0 | none | polymelamine | + |
| Comparative Example 47 |  |  |  |  |  |  | polyurea | + |
| Comparative Example 48 |  |  |  |  |  |  | polyxylene | + |
| Comparative Example 49 | 4-4 | none | none | 0 | 0 | none | polymelamine | + |
| Comparative Example 50 |  |  |  |  |  |  | polyurea | + |
| Comparative Example 51 |  |  |  |  |  |  | polyxylene | + |

TABLE 5-continued

|  | Amount of eluted dye | Variation coefficient of dye-resin particle [%] | Evaluation 1: Bleeding of dye in HER2-stained image | Evaluation 2: Brightness of HER2-stained image | Evaluation 3: Measurement of bright spots |
|---|---|---|---|---|---|
| Comparative Example 40 | 127 | 10 | DD | DD<br>not measurable | DD<br>not measurable |
| Comparative Example 41 | 127 | 14 | DD | DD<br>not measurable | DD<br>not measurable |
| Comparative Example 42 | 565 | 11 | DD | DD<br>not measurable | DD<br>not measurable |
| Comparative Example 43 | 74 | 10 | DD | DD<br>not measurable | DD<br>not measurable |
| Comparative Example 44 | 74 | 10 | DD | DD<br>not measurable | DD<br>not measurable |
| Comparative Example 45 | 154 | 11 | DD | DD<br>not measurable | DD<br>not measurable |
| Comparative Example 46 | 94 | 11 | DD | DD<br>not measurable | DD<br>not measurable |
| Comparative Example 47 | 94 | 10 | DD | DD<br>not measurable | DD<br>not measurable |
| Comparative Example 48 | 244 | 12 | DD | DD<br>not measurable | DD<br>not measurable |
| Comparative Example 49 | 83 | 12 | DD | DD<br>not measurable | DD<br>not measurable |
| Comparative Example 50 | 83 | 11 | DD | DD<br>not measurable | DD<br>not measurable |
| Comparative Example 51 | 189 | 13 | DD | DD<br>not measurable | DD<br>not measurable |

(Discussion)

Since the fluorescent dye had no electric charge and neither ionic bond nor covalent bond was formed between the fluorescent dye and the resin, the amount of the eluted dye was large and the bleeding of the dye in the post-staining fluorescence observation was prominent. Consequently, the measurement of the bright spots and the like were difficult (Comparative Examples 40 to 51).

Dye-Resin Particles with Variation Coefficient of 15% or Less, in which Negatively Charged Fluorescent Dye is Immobilized on Negatively Charged Resin Comparative Example 52 (Polyphenol Particle Encapsulating Compound 1-1)

The production of dye-resin particles, preparation of streptavidin, morphological staining and the like were carried out in the same manner as in Example 1, except that a polyphenol resin having the same negative charge as that of the fluorescent dye (Compound 1-1) was used in place of the positively charged polymelamine resin (see Table 6).

Comparative Example 53 (Polyxylene Particle Encapsulating Compound 1-1)

The production of dye-resin particles, preparation of streptavidin, morphological staining and the others were carried out in the same manner as in Example 1, except that a negatively charge polyxylene resin was used in place of the positively charged polymelamine resin (see Table 6).

Comparative Example 54, 56, 58, 60, 62 and 64 (Polyphenol Particles Encapsulating Compounds 1-2 to 1-7)

The production of dye-resin particles and the others were carried out in the same manner as in Comparative Example 52, except that Compound 1-1 was changed to Compound 1-2 (Comparative Example 54), Compound 1-3 (Comparative Example 56), Compound 1-4 (Comparative Example 58), Compound 1-5 (Comparative Example 60), Compound 1-6 (Comparative Example 62) or Compound 1-7 (Comparative Example 64).

In other words, Comparative Examples 52, 54, 58, 60, 62 and 64 are examples where dye-resin particles having a variation coefficient of 15% or less, in which a fluorescent dye (Compounds 1-1 to 1-7) having the same negative charge as that of polyphenol resin particles was encapsulated in the negatively charged polyphenol resin particles, were produced to perform immunohistological staining, morphological staining, evaluation of a tissue image and the others.

Comparative Examples 55, 57, 59, 61, 63 and 65 (Polyxylene Particles Encapsulating Compounds 1-2 to 1-7)

The production of dye-resin particles and the others were carried out in the same manner as in Comparative Example 53, except that Compound 1-1 was changed to Compound 1-2 (Comparative Example 55), Compound 1-3 (Comparative Example 57), Compound 1-4 (Comparative Example 59), Compound 1-5 (Comparative Example 61), Compound 1-6 (Comparative Example 63) or Compound 1-7 (Comparative Example 65).

In other words, Comparative Examples 53, 55, 57, 59, 61, 63 and 65 are examples where dye-resin particles having a variation coefficient of 15% or less, in which a fluorescent dye (Compounds 1-1 to 1-7) having the same negative charge as that of polyxylene resin particles was encapsulated in the negatively charged polyxylene resin particles, were produced to perform immunohistological staining, morphological staining, evaluation of a tissue image and the others.

TABLE 6

| | Dye code (Compound) | Dye electric charge | Substituent of dye | Dye molecular weight | Number of substituents | Dye molecular weight/Number of charged substituents | Resin type | Resin charge |
|---|---|---|---|---|---|---|---|---|
| Comparative Example 52 | 1-1 | − | sulfo group | 578 | 2 | 289 | polyphenol | − |
| Comparative Example 53 | | | | | | | polyxylene | − |
| Comparative Example 54 | 1-2 | − | sulfo group | 693 | 4 | 173 | polyphenol | − |
| Comparative Example 55 | | | | | | | polyxylene | − |
| Comparative Example 56 | 1-3 | − | sulfo group | 924 | 4 | 231 | polyphenol | − |
| Comparative Example 57 | | | | | | | polyxylene | − |
| Comparative Example 58 | 1-4 | − | sulfo group | 397 | 2 | 199 | polyphenol | − |
| Comparative Example 59 | | | | | | | polyxylene | − |
| Comparative Example 60 | 1-5 | − | sulfo group | 436 | 2 | 218 | polyphenol | − |
| Comparative Example 61 | | | | | | | polyxylene | − |
| Comparative Example 62 | 1-6 | − | sulfo group | 472 | 3 | 157 | polyphenol | − |
| Comparative Example 63 | | | | | | | polyxylene | − |
| Comparative Example 64 | 1-7 | − | sulfo group | 1,398 | 4 | 350 | polyphenol | − |
| Comparative Example 65 | | | | | | | polyxylene | − |

| | Amount of eluted dye | Variation coefficient of dye-resin particle [%] | Evaluation 1: Bleeding of dye in HER2-stained image | Evaluation 2: Brightness of HER2-stained image | Evaluation 3: Measurement of bright spots |
|---|---|---|---|---|---|
| Comparative Example 52 | 256 | 9 | DD | DD | DD |
| Comparative Example 53 | 152 | 11 | DD | not measurable | not measurable |
| Comparative Example 54 | 188 | 10 | DD | DD | DD |
| Comparative Example 55 | 175 | 11 | DD | not measurable | not measurable |
| Comparative Example 56 | 208 | 10 | DD | DD | DD |
| Comparative Example 57 | 168 | 12 | DD | not measurable | not measurable |
| Comparative Example 58 | 143 | 11 | DD | DD | DD |
| Comparative Example 59 | 121 | 13 | DD | not measurable | not measurable |
| Comparative Example 60 | 101 | 10 | DD | DD | DD |
| Comparative Example 61 | 96 | 12 | DD | not measurable | not measurable |
| Comparative Example 62 | 136 | 10 | DD | DD | DD |
| Comparative Example 63 | 124 | 12 | DD | not measurable | not measurable |
| Comparative Example 64 | 189 | 10 | DD | DD | DD |
| Comparative Example 65 | 156 | 12 | DD | not measurable | not measurable |

(Discussion)

When the fluorescent dye and the resin had the same negative change, since they electrically repelled each other, immobilization of the fluorescent dye on the resin was not attained by ionic bonding or covalent bonding. Consequently, bleeding of the fluorescent dye occurred in the post-staining fluorescence observation, making it difficult to measure the brightness and the bright spots (Comparative Examples 52 to 65).

Dye-Resin Particles with Variation Coefficient of 15% or Less, in which Positively Charged Fluorescent Dye is Immobilized on Positively Charged Resin Comparative Example 66 (Polymelamine Particles Encapsulating Compound 1-8)

The production of dye-resin particles, tissue staining and the others were carried out in the same manner as in Example 1, except that a fluorescent dye (Compound 1-8) having the same positive charge as that of the resin was used in place of the negatively charged fluorescent dye (Compound 1-1) (see Table 7).

Comparative Example 67 (Particles Encapsulating Compound 1-8)

The production of dye-resin particles, tissue staining and the others were carried out in the same manner as in Example 2, except that Compound 1-8 was used in place of Compound 1-1 (see Table 7).

Comparative Example 68 (Polyxylene Particles Encapsulating Compound 1-8)

The production of dye-resin particles, tissue staining and the like were carried out in the same manner as in Example 3, except that Compound 1-8 was used in place of Compound 1-1 (see Table 7).

TABLE 7

| | Dye | | | | | | | | Variation coefficient of dye-resin particle [%] | Evaluation | | |
|---|---|---|---|---|---|---|---|---|---|---|---|---|
| | Dye code (Compound) | Dye electric charge | Substituent of dye | Dye molecular weight | Number of substituents | Dye molecular weight/Number of charged substituents | Resin type | Resin charge | Amount of eluted dye | | Evaluation 1: Bleeding of dye in HER2-stained image | Evaluation 2: Brightness of HER2-stained image | Evaluation 3: Measurement of bright spots |
| Comparative Example 66 | 1-8 | + | ammonium group | 1,366 | 4 | 342 | poly-melamine | + | 110 | 14 | DD | DD not measurable | DD not measurable |
| Comparative Example 67 | | | | | | | poly-urea | + | 124 | 12 | DD | DD not measurable | DD not measurable |
| Comparative Example 68 | | | | | | | poly-xylene | + | 152 | 11 | DD | DD not measurable | DD not measurable |

(Discussion)

When the fluorescent dye and the resin had the same positive change, since they electrically repelled each other, immobilization of the fluorescent dye on the resin was not attained by ionic bonding. Consequently, bleeding of the fluorescent dye occurred in the post-staining fluorescence observation, making it difficult to measure the brightness and the bright spots (Comparative Examples 66 to 68).

TABLE 8

| | Dye code (Compound) | Dye electric charge | Substituent of dye | Dye molecular weight | Number of substituents | Dye molecular weight/Number of charged substituents | Resin type |
|---|---|---|---|---|---|---|---|
| Example 38 | 1-1 | − | sulfo group | 578 | 2 | 289 | polymelamine |
| Example 39 | 1-2 | − | sulfo group | 693 | 4 | 173 | polymelamine |
| Example 40 | 1-3 | − | sulfo group | 924 | 4 | 231 | polymelamine |
| Example 41 | 1-4 | − | sulfo group | 397 | 2 | 199 | polymelamine |
| Example 42 | 1-5 | − | carboxyl group | 436 | 2 | 218 | polymelamine |
| Example 43 | 1-6 | − | sulfo group | 472 | 3 | 157 | polymelamine |
| Example 44 | 1-7 | − | sulfo group | 1,399 | 4 | 350 | polymelamine |
| Example 45 | 2-1 | − | carboxyl group | 430 | 1 | 430 | polymelamine |
| Example 46 | 2-2 | − | sulfo group | 605 | 1 | 605 | polymelamine |
| Example 47 | 3-1 | none | amide bond (covalent bond) | 316 | 2 | 316 | polymelamine |
| Example 48 | 3-2 | none | amide bond (covalent bond) | 439 | 4 | 439 | polymelamine |

TABLE 8-continued

| | Resin charge | Amount of eluted dye | Variation coefficient of dye-resin particle [%] | Evaluation 1: Bleeding of dye in HER2-stained image | Evaluation 2: Brightness of HER2-stained image | Evaluation 3: Measurement of bright spots |
|---|---|---|---|---|---|---|
| Example 38 | + | 5 | 3 | CC | BB | BB |
| Example 39 | + | 1 | 3 | BB | BB | BB |
| Example 40 | + | 1 | 4 | BB | BB | BB |
| Example 41 | + | 1 | 5 | BB | BB | BB |
| Example 42 | + | 9 | 8 | CC | CC | BB |
| Example 43 | + | 1 | 5 | BB | BB | BB |
| Example 44 | + | 0 | 4 | BB | AA | BB |
| Example 45 | + | 20 | 5 | CC | CC | BB |
| Example 46 | + | 19 | 5 | CC | CC | BB |
| Example 47 | + | 0 | 5 | BB | CC | BB |
| Example 48 | + | 0 | 5 | BB | CC | BB |

Example 38 (Polymelamine Particle Encapsulating Compound 1-1)

The same procedures were performed as in Example 1, except that the time of the centrifugation performed in the process of washing the dye-resin particles with pure water was shortened from 15 minutes to 10 minutes; and, after repeating the operations of centrifugation, supernatant removal and re-dispersion in ultrapure water five times as in Example 1, the resultant was subjected to another 1-minute centrifugation to remove the precipitates.

Examples 39 to 48 (Polymelamine Particles Encapsulating Compounds 1-2 to 3-2)

The production of dye-resin particles and the others were carried out in the same manner as in Example 38, except that Compound 1-1 was changed to Compound 1-2 (Example 39), Compound 1-3 (Example 40), Compound 1-4 (Example 41), Compound 1-5 (Example 42), Compound 1-6 (Example 43), Compound 1-7 (Example 44), Compound 2-1 (Example 45), Compound 2-2 (Example 46), Compound 3-1 (Example 47) or Compound 3-2 (Example 48).

Thus far, the present invention have been described based on embodiments and examples thereof; however, the present invention is not restricted to these embodiments and examples, and design modifications and the like can be made as long as they do not deviate from the gist of the present invention.

The invention claimed is:

1. A staining agent for tissue staining, comprising, as a staining component, dye-resin particles containing thermosetting resin particles and a fluorescent dye immobilized on said thermosetting resin particles, wherein
said thermosetting resin particles contain a substituent having an electric charge opposite to that of said fluorescent dye and form an ionic bond and optionally a covalent bond with said fluorescent dye, and
said dye-resin particles have a particle size variation coefficient of 15% or less.

2. The staining agent for tissue staining according to claim 1, wherein said fluorescent dye is encapsulated in said thermosetting resin particles.

3. The staining agent for tissue staining according to claim 1, wherein substituents contributing to said ionic bond are a negatively charged substituent for said fluorescent dye and a positively charged substituent for said thermosetting resin particles.

4. The staining agent for tissue staining according to claim 1, wherein the electric charge of said fluorescent dye as a whole and that of said thermosetting resin particles as a whole are the same as the electric charge of the respective substituents contributing to said ionic bond.

5. The staining agent for tissue staining according to claim 1, wherein, in said fluorescent dye, the ratio, the molecular weight of said fluorescent dye per molecule/the number of charged substituents, is less than 400.

6. The staining agent for tissue staining according to claim 3, wherein said fluorescent dye contains at least two negatively charged substituents per molecule.

7. The staining agent for tissue staining according to claim 3, wherein
said positively charged substituent is an amino group, and
said negatively charged substituent is a sulfo group or a carboxyl group.

8. The staining agent for tissue staining according to claim 6, wherein at least one of said negatively charged substituents of said fluorescent dye is a sulfo group.

9. The staining agent for tissue staining according to claim 1, wherein said fluorescent dye is rhodamine, BODIPY, squarylium or an aromatic hydrocarbon-based dye molecule.

10. The staining agent for tissue staining according to claim 9, wherein
said thermosetting resin particles are formed using melamine, and
said fluorescent dye is rhodamine or an aromatic hydrocarbon-based dye molecule.

11. The staining agent for tissue staining according to claim 1, wherein said thermosetting resin particles and said fluorescent dye form the ionic bond and the covalent bond therebetween, and wherein the covalent bond is any one of an amide bond, an ester bond, an ether bond and a C—N bond.

12. The staining agent for tissue staining according to claim 1, wherein
said thermosetting resin comprises a structural unit formed from at least one monomer selected from the group consisting of melamine, urea, guanamine, phenol, xylene and derivatives thereof, and
at least some of the hydrogens contained in said structural unit are substituted with a charged substituent.

13. A tissue staining kit, comprising the staining agent for tissue staining according to claim 1 as a component.

14. The staining agent for tissue staining according to claim 1, wherein said dye-resin particles have an average particle size of 50 to 200 nm.

* * * * *